(12) United States Patent
Hansel et al.

(10) Patent No.: US 9,221,877 B2
(45) Date of Patent: Dec. 29, 2015

(54) CURCUMIN CONJUGATES FOR TREATING AND PREVENTING CANCERS

(75) Inventors: William Hansel, Baton Rouge, LA (US); Sita Aggarwal, Hammond, LA (US); Robert P. Hammer, Acton, MA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 334 days.

(21) Appl. No.: 13/119,549

(22) PCT Filed: Sep. 16, 2009

(86) PCT No.: PCT/US2009/057141
§ 371 (c)(1),
(2), (4) Date: May 31, 2011

(87) PCT Pub. No.: WO2010/033580
PCT Pub. Date: Mar. 25, 2010

(65) Prior Publication Data
US 2011/0263500 A1    Oct. 27, 2011

Related U.S. Application Data

(60) Provisional application No. 61/121,019, filed on Dec. 9, 2008, provisional application No. 61/098,414, filed on Sep. 19, 2008.

(51) Int. Cl.
*A61K 38/00* (2006.01)
*A61K 47/48* (2006.01)
*C07K 7/23* (2006.01)

(52) U.S. Cl.
CPC ............ *C07K 7/23* (2013.01); *A61K 47/48246* (2013.01); *A61K 38/00* (2013.01)

(58) Field of Classification Search
CPC ............ A61K 47/48246; A61K 38/09; A61K 36/9066; C07K 7/23
See application file for complete search history.

(56) References Cited

U.S. PATENT DOCUMENTS

| | | | |
|---|---|---|---|
| 5,891,415 A | 4/1999 | Alkhazov et al. | 423/573.1 |
| 5,891,924 A | 4/1999 | Aggarwal | 514/679 |
| 6,635,740 B1 | 10/2003 | Enright et al. | 530/324 |
| 6,790,979 B2 * | 9/2004 | Lee et al. | 560/53 |
| 2007/0270464 A1 * | 11/2007 | Liotta et al. | 514/318 |

FOREIGN PATENT DOCUMENTS

| WO | WO/02/02582 | 1/2002 |
|---|---|---|
| WO | WO 2008045534 A2 * | 4/2008 |

OTHER PUBLICATIONS

Johnson et al., "Curcumin for chemoprevention of colon cancer", Cancer Letters, 2001, pp. 170-181.*
Chatzistamou et al. ("Effective Treatment of Metastatic MDA-MB-435 Human Estrogen-independent Breast Carcinomas with a Targeted Cytotoxic Analogue of Luteinizing Hormone-releasing Hormone AN-2071", Clinical Cancer Research; 2000; pp. 4158-4165).*
Vareed et al. ("Pharmacokinetics of Curcumin Conjugate Metabolites in Healthy Human Subjects", Cancer Epidemiol Biomarkers Prev;2008;pp. 1411-1417).*
Aggarwal et al., "[DLys6]-luteinizing hormone releasing hormone—curcumin conjugate inhibits pancreatic cancer cell growth in vitro and in vivo", International Journal of Cancer, 2011, pp. 1611-1623.*
Lin, "Design, Synthesis and Bio-Evaluation of New Curcumin Analogs as Potential Drug Candidates for the Treatment of Prostate Cancer", ProQuest Information and Learning Company, 2006, document pp. 1-126.*
Lin, "Design, Synthesis and Bio-Evaluation of New Curcumin Analogs as Potential Drug Candidates for the Treatment of Prostate Cancer", ProQuest Information and Learning Company, 2006, pp. 1-126.*
Aggarwal, S. et al., "Curcumin (diferuloylmethane) down-regulates expression of cell proliferation and antiapoptotic and metastatic gene products through suppression of kappa B alpha kinase and Akt activation," *Mol. Pharmacol.*, vol. 69, pp. 195-206 (2006).
Aggarwal, S. et al., "Inhibition of growth and survival of human head and neck squamous cell carcinoma cells by curcumin via modulation of nuclear factor-kappaB signaling," Int. J. Cancer, vol. 111, pp. 679-692 (2004).
Chegini, N. et al., "Gonadotropin-releasing hormone (GnRH) and GnRH receptor gene expression in human myometrium and leiomyomata and the direct action of GnRH analogs on myometrial smooth muscle cells and interaction with ovarian steroids in vitro," *J. Clin. Endocrin. Metab.*, vol. 81, pp. 3215-3221 (1996).
Chuang, S. et al., "Curcumin-containing diet inhibits diethylnitrosamine-induced murine hepatocarcinogenesis," *Carcinogenesis*, vol. 21, pp. 331-335 (2000).
Dharap, S. et al., "Tumor-specific targeting of an anticancer drug delivery system by LHRH peptide," PNAS, vol. 102, No. 36, pp. 12962-12967 (2005).
Dhillon, N. et al., "Phase II clinical trial of curcumin in patients with advanced pancreatic cancer," *J. Clin. Onco.*, vol. 24, pp. 14151 ff (2006).
Dubey, S. et al., "Design, synthesis and characterization of some bioactive conjugates of curcumin with glycine, glutamic acid, valine and demethylenated piperic acid and study of their antimicrobial and antiproliferative properties," *Eur. J. Medicinal Chem.*, vol. 43, pp. 1837-1846 (2008).

(Continued)

*Primary Examiner* — Karlheinz R Skowronek
*Assistant Examiner* — Lianko Garyu
(74) *Attorney, Agent, or Firm* — John H. Runnels

(57) ABSTRACT

Conjugating LHRH to curcumin (LHRH-Curcumin) substantially enhances the bioavailability of curcumin, targets it to cells expressing LHRH receptors, facilitates intravenous administration, and increases the anti-cancer efficacy of curcumin. The conjugate may be used against cancer cells that express the LHRH receptor: pancreas, prostate, breast, testicular, uterine, ovarian, melanoma. LH-Curcumin conjugates may be used against cancer cells that express the LH receptor: prostate, breast, ovary, testis, uterus, pancreas, and melanoma.

1 Claim, 8 Drawing Sheets

(56) References Cited

OTHER PUBLICATIONS

Dutta, S. et al., "Enhanced antioxidant activities of metal conjugates of curcumin derivatives," *Metal Based Drugs*, vol. 8, pp. 183-188 (2001).

Emons, G. et al., "Growth Inhibitory Actions of Analogues of Luteinizing Hormone Releasing Hormone on Tumor Cells," TEM, vol. 8, No. 9, pp. 355-362 (1997).

Emons, G. et al., "High Affinity Binding and Direct Antiproliferative Effects of LHRH Analogues in Human Ovarian Cancer Cell Lines," Cancer Res., vol. 53, pp. 5439-5446 (1993).

Friess, H. et al., "LH-RH receptors in the human pancreas. Basis for antihormonal treatment in ductal carcinoma of the pancreas," *Int. J. Gastrointestinal Cancer*, vol. 10, pp. 151-159 (1991).

Grundker, C. et al., "Biology of the Gonadotropin-Releasing Hormone System in Gynecological Cancers," Euro. J. of Endoc., vol. 146, pp. 1-14 (2002).

Halmos, G. et al., "High Incidence of Receptors for Luteinizing Hormone-Releasing Hormone (LHRH) and LHRH Receptor Gene Expression in Human Prostate Cancers," J. of Urology, vol. 163, pp. 623-629.

Hansel, W. et al., "Destruction of breast cancers and their metastases by lytic peptide conjugates in vitro and in vivo," *Mol. Cell. Endocrinol.*, vol. 260-262, pp. 183-189 (2007).

Hansel, W. et al., "Conjugates of lytic peptides and LHRH or BetaCG target and cause necrosis of prostate cancers and metastases," *Mol. Cell. Endocrinol.*, vol. 269, pp. 26-33 (2007).

Huang, M. et al., "Effect of dietary curcumin and dibenzoylmethane on formation of 7,12-dimethylbenz[a]anthracene-induced mammary tumors and lymphomas/leukemias in Sencar mice," *Carcinogenesis*, vol. 19, pp. 1697-700 (1998).

Ikeda, M. et al., "Gene Expression of Gonadotrophin-Releasing Hormone, but not its receptor, in human endometrium and decidua," Mol. and Cellular Endocrinology, vol. 135, pp. 165-168 (1997).

Imai, A. et al., "Fas and Fas Ligand System May Mediate Antiproliferative Activity of Gonadotropin-Releasing Hormone Receptor in Endometrial Cancer Cells," Int'l J. of Oncology, vol. 13, pp. 97-100 (1998).

Kim, J. et al., "Chemopreventive effects of carotenoids and curcumins on mouse colon carcinogenesis after 1,2-dimethylhydrazine initiation," *Carcinogenesis*, vol. 19, pp. 81-85 (1998).

Kunnumakkara, A. et al., "Curcumin potentiates antitumor activity of gemcitabine in an orthotopic model of pancreatic cancer through suppression of proliferation, angiogenesis, and inhibition of nuclear factor-kappaB-regulated gene products," *Cancer Res.* vol. 67, pp. 3853-3861 (2007).

Kuo, M. et al., "Curcumin, an antioxidant and anti-tumor promoter, induces apoptosis in human leukemia cells," *Biochim. Biophys. Acta*, vol. 1317, pp. 95-100 (1996).

Lee et al., "Pharmacokinetics and Pharmacodynamics of Phor21-βCG(ala), a Lytic Peptide Conjugate," *J. Pharmacokinetics and Pharmacodynamics*, vol. 60, pp. 1-8 (2008).

Leuschner, C. et al., "Membrane disrupting lytic peptides for cancer treatments," *Curr. Pharm. Des.*, vol. 10, pp. 2299-310 (2004).

Leuschner, C. et al., "Targeted Destruction of Androgen-Sensitive and -Insensitive Prostate Cancer Cells and Xenografts Through Luteinizing Hormone Receptors," The Prostate, vol. 46, pp. 116-125 (2001).

Leuschner, C. et al., "Targeting breast and prostate cancers through their hormone receptors," *Biol. Reprod.*, vol. 73, pp. 860-865 (2005).

Li, L. et al., "Liposome-Encapsulated Curcumin," Cancer, vol. 104, No. 6, pp. 1322-1331 (2005).

Limtrakul, P. et al., "Inhibitory effect of dietary curcumin on skin carcinogenesis in mice," *Cancer Lett.*, vol. 116, pp. 197-203 (1997).

Marinaccio, M. et al., "The estimation of LHRH receptors in the tissue of human leiomyoma, myometrium and endometrium," *Minerva Ginecol.*, vol. 46, pp. 519-526 (1994, English language abstract).

Mishra, S. et al., "Design, development and synthesis of mixed bioconjugates of piperic acid-glycine, curcumin-glycine/alanine and curcumin-glycine-/alanine and curcumin-glycine-piperic acid and their antibacterial and antifungal properties," Bioorganic & Med. Chem., vol. 13, pp. 1477-1486 (2005).

Mishra, S. et al., "Differential apoptotic and redox regulatory activities of curcumin and its derivatives," *Free Radical Biology & Medicine*, vol. 38, pp. 1353-1360 (2005).

Nagy, A. et al., "Targeting Cytotoxic Conjugates of Somatostatin, Luteinizing Hormone-Releasing Hormone and Bombesin to Cancers Expressing Their Receptors: A 'Smarter' Chemotherapy," Current Pharmaceutical Design, vol. 11, No. 9, pp. 1167-1180 (2005).

Schally, A. et al., "Cancer Chemotherapy Based on Targeting of Cytotoxic Peptide Conjugates to Their Receptors on Tumors," Euro. J. of Endoc., vol. 141, pp. 1-14 (1999).

Shim, J. et al., "Hydrazinocurcumin, a novel synthetic curcumin derivative, is a potent inhibitor of endothelial cell proliferation," *Bioorganic & Medicinal Chemistry*, vol. 10, pp. 2987-2992 (2002).

Srkalovic, G. et al., "Presence and Characteristics of Receptors for [D-Trp$^6$]Luteinizing Hormone Releasing Hormone and Epidermal Growth Factor in Human Ovarian Cancer," Int'l J. of Oncology, vol. 12, pp. 489-498 (1998).

Szende, B. et al., "Localization of receptors for luteininizing hormone-releasing hormone in pancreatic and mammary cancer cells," *Proc. Natl. Acad. Sci. USA*, vol. 88, pp. 4153-4156 (1991).

Wieser, F. et al., "Evolution of Medical Treatment for Endometriosis: Back to the Roots?" Human Repro. Update, vol. 13, No. 5, pp. 487-499 (2007).

Wirth, M. et al., "Lectin-Mediated Drug Delivery: Influence of Mucin on Cytoadhesion of Plant Lectins in vitro," J. of Controlled Release, vol. 79, pp. 183-191 (2002).

Valentine, S. et al., "Curcumin Modulates Drug Metabolizing Enzymes in the Female Swiss Webster Mouse," Life Sciences, vol. 78, pp. 2391-2398 (2006).

Zambre, A.P. et al., "Novel Curcumin Analogs Targeting TNF-Induced NF-κB Activation and Proliferation in Human Leukemic KBM-5 Cells," Bioorganic & Med. Chem., vol. 14, pp. 7196-7204 (2006).

Somasundaram, Sivagurunathan et al., "Dietary Curcumin Inhibits Chemotherapy-induced Apoptosis in Models of Human Breast Cancer," Cancer Res, vol. 62, pp. 3868-3875 (2002).

Rai, Diwakar et al., "Design and Development of Curcumin Bioconjugates as Antiviral Agents," Oxford Univ. Press, Nucleic Acids Symposium Series No. 52, pp. 599-600 (2008).

\* cited by examiner

Curcumin analogues

Curcumin analogues

US 9,221,877 B2

CURCUMIN CONJUGATES FOR TREATING AND PREVENTING CANCERS

This is the United States national stage of international application PCT/US2009/057141, international filing date Sep. 16, 2009, which claims the benefit of the Sep. 19, 2008 filing date of U. S. provisional patent application Ser. No. 61/098,414, and of the Dec. 9, 2008 filing date of U.S. provisional patent application Ser. No. 61/121,019 under 35 U.S.C. §119(e).

TECHNICAL FIELD

This invention pertains to treating and preventing cancers.

BACKGROUND ART

Pancreatic cancer is highly lethal. It has been estimated that 37,170 new cases and 33,370 deaths resulted from pancreatic cancer in the United States in 2007. Pancreatic cancer has one of the worst prognoses of all human malignancies. Existing treatments, such as surgical resection and chemotherapy, have poor survival rates. The 5-year survival rate for patients diagnosed after the occurrence of metastases is very low, and has not improved since 1973. Pancreatic cancer is a multistep, progressive disease characterized by genetic abnormalities, altered signaling pathways, and loss of cellular regulatory functions. Metastatic cells in bone, lungs, lymph nodes, and other organs cause recurrent cancer and are the major cause of death. An effective targeted therapy could be of great benefit for patients with advanced or metastatic tumors from pancreatic cancer.

Three distinct precursor lesions of pancreatic cancers have been identified: mucinous cystic neoplasms, intraductal papillary mucinous neoplasms (IPMNs), and pancreatic intraepithelial neoplasia (PanINs). PanINs progress from early lesions, PanIN-1A and1B (hyperplasia), through PanIN-2 lesions, and then to PanIN-3 lesions (carcinoma in situ) (2). Pancreatic ductal adenocarcinoma (PDAC) accounts for 90 percent of pancreatic cancers.

The molecular mechanisms underlying pancreatic cancers have been extensively investigated. Several tyrosine kinase growth factor receptors and their ligands are overexpressed, including epidermal growth factor (EGF), epidermal growth factor receptor (EGFR-1) and its ligands, transforming growth factor-alpha (TGF-α), the TGF-β superfamily of serine-threonine kinase receptors and their ligands, the fibroblast growth factor family, the insulin-like growth factor family, hepatocyte growth factor, platelet-derived growth factor, and vascular endothelial growth factor. This overexpression influences tumor cell growth, differentiation, invasion, metastasis, and angiogenesis, factors that are associated with tumor aggressiveness and short survival periods even following tumor resection.

Gonadotropin-releasing hormone (GnRH, a decapeptide, also called luteinizing hormone releasing hormone or LHRH), and the LHRH receptor molecule (LHRHR) are best known for their functions in reproduction. They also play a role in the negative autocrine/paracrine regulatory system of cell proliferation in several malignant tumors, including cancers of the endometrium, ovary, breast, prostate, endometrium, and melanomas. About 50% of breast cancers and 80% of ovarian and endometrial cancers express high affinity binding sites for LHRH. In these cancers in vitro proliferation has been inhibited by agonist or antagonist analogues of LHRH. The role of LHRH and LHRHR in pancreatic cancer has received less attention See H. Friess et al., "LH-RH receptors in the human pancreas. Basis for antihormonal treatment in ductal carcinoma of the pancreas," *Int. J. Gastrointestinal Cancer*, vol. 10, pp. 151-159 (1991); and B. Szende et al., "Localization of receptors for luteininizing hormone-releasing hormone in pancreatic and mammary cancer cells," *Proc. Natl. Acad. Sci. USA*, vol. 88, pp. 4153-4156 (1991).

A major problem in most forms of cancer chemotherapy is the severe toxicity most such drugs also have against rapidly-dividing cells in healthy tissues. These side effects often result in dose reduction, treatment delay or discontinuance of therapy. Targeted drug delivery systems have been developed to try to circumvent these side effects, using targeting agents such as receptor ligands, sugars, lectins, antibodies, antibody fragments, hormones, and hormone analogues. For example, conjugates of lytic peptides with either LH or LHRH (or analogs) have been used against cancers, such as breast cancers and prostate cancers, that express LH receptor or LHRH receptor on their membranes. See C. Leuschner et al., "Membrane disrupting lytic peptides for cancer treatments," *Curr. Pharm. Des.*, vol. 10, pp. 2299-310 (2004); U.S. Pat. No. 6,635,740; W. Hansel et al., "Destruction of breast cancers and their metastases by lytic peptide conjugates in vitro and in vivo," *Mol. Cell. Endocrinol.*, vol. 260-262, pp. 183-9 (2007); U.S. Pat. No. 6,635,740; and C. Leuschner et al., "Targeting breast and prostate cancers through their hormone receptors," *Biol. Reprod.*, vol. 73, pp. 860-5 (2005).

Numerous mechanisms have been suggested for the effects of LHRH and LHRHR. One proposed mechanism involves activation of nuclear factor-kappa B (NF-kB) in ovarian cancer cells. NF-kB is a regulatory transcription factor involved in controlling cell growth, differentiation, survival, and cell cycle progression. In normal cells NF-kB is not constitutively expressed, except in proliferating T cells, B-cells, thymocytes, monocytes, and astrocytes. There is evidence to suggest that NF-kB plays a role in the growth and chemoresistance of pancreatic cancer: (1) NF-kB has been found to be constitutively active in pancreatic cancer cells, but not in immortalized, nontumorigenic pancreatic ductal epithelial cells. (2) Active NF-kB has been reported in pancreatic cancer xenografts in mice. (3) NF-kB has been reported to promote pancreatic cancer growth by inhibiting apoptosis. (4) The NF-kB-mediated gene product cyclin D1 is overexpressed in human pancreatic cancer tissue, and has been inversely correlated with patient survival. (5) NF-kB has been associated with gemcitabine resistance in pancreatic cancer.

There is an unfilled need for strong inhibitors of NF-kB to treat or prevent pancreatic cancer and other cancers in which the cancer cell membranes express receptors for one or more of LHRH, LH, or CG.

Epidemiologic and animal studies have shown that compounds that are naturally present in some foods can help prevent cancer. Some of these compounds have further shown significant anti-tumor activity, both in vitro and in preclinical testing. There is an increasing interest in plant-derived chemicals that have anti-cancer activity with low toxicity. Curcumin (diferuloylmethane), a phytochemical present in turmeric (*Curcumin longa*), has been reported to have potent anti-proliferative and pro-apoptotic effects on cancer cells in vitro. In murine models, curcumin has suppressed carcinogenesis of the skin, the breast, the colon, and the liver. Curcumin has been shown to suppress NF-kB activity. Curcumin is pharmacologically safe, but it has low solubility in water and therefore has poor bioavailability by oral administration, and cannot be administered intravenously. Orally-administered curcumin has, nevertheless, been reported to potentiate the effect of the chemotherapeutic agent Gemcitabine in mice pancreatic cancer models. See M. Kuo et al., "Curcumin, an antioxidant and anti-tumor promoter, induces apoptosis in human leukemia cells," *Biochim. Biophys. Acta*, vol. 1317, pp. 95-100 (1996); S. Aggarwal et al., "Inhibition of growth and survival of human head and neck squamous cell carcinoma cells by curcumin via modulation of nuclear factor-kappaB signaling," *Int. J. Cancer*, vol. 111, pp. 679-92 (2004); P. Limtrakul et al., "Inhibitory effect of dietary curcumin on skin carcinogenesis in mice," *Cancer Lett.*, vol. 116, pp. 197-203 (1997); M. Huang et al., "Effect of dietary curcumin and dibenzoylmethane on formation of 7,12-dimethylbenz[a]anthracene-induced mammary tumors and lymphomas/leukemias in Sencar mice," *Carcinogenesis*, vol. 19, pp. 1697-700 (1998); J. Kim et al., "Chemopreventive effects of carotenoids and curcumins on mouse colon carcinogenesis after 1,2-dimethylhydrazine initiation," *Carcinogenesis*, vol. 19, pp. 81-5 (1998); S. Chuang et al., "Curcumin-containing diet inhibits diethylnitrosamine-induced murine hepatocarcinogenesis," *Carcinogenesis*, vol. 21, pp. 331-5 (2000); S. Aggarwal et al., "Curcumin (diferuloylmethane) down-regulates expression of cell proliferation and antiapoptotic and metastatic gene products through suppression of kappa B alpha kinase and Akt activation," *Mol. Pharmacol.*, vol. 69, pp. 195-206 (2006); A. Kunnumakkara et al., "Curcumin potentiates antitumor activity of gemcitabine in an orthotopic model of pancreatic cancer through suppression of proliferation, angiogenesis, and inhibition of nuclear factor-kappaB-regulated gene products," *Cancer Res.* vol. 67, pp. 3853-61 (2007).

In Phase II clinical trials in patients with advanced pancreatic cancer, orally-administered curcumin was reported to have only limited effect, and to have poor bioavailability. "Clinical biological activity" was reported for only 2 of 21 patients, consisting of a brief but marked period of tumor regression in one patient, and a "stabilization" of the disease for 18 months in the other patient. See N. Dhillon et al., "Phase II clinical trial of curcumin in patients with advanced pancreatic cancer," *J. Clin. Onco.*, vol. 24, pp. 14151 ff (2006); see also published United States patent application publication no. 2007/0270464.

S. Mishra et al., "Design, development and synthesis of mixed bioconjugates of piperic acid-glycine, curcumin-glycine/alanine and curcumin-glycine-piperic acid and their antibacterial and antifungal properties," *Bioorganic & Medicinal Chemistry*, vol. 13, pp. 1477-1486 (2005) discloses the synthesis of the curcumin conjugates named in the paper's title, and the use of those conjugates against certain bacteria and fungi.

S. Mishra et al., "Differential apoptotic and redox regulatory activities of curcumin and its derivatives," *Free Radical Biology & Medicine*, vol. 38, pp. 1353-1360 (2005) discloses several derivatives of curcumin, and the use of those derivatives to induce apoptosis in rat histiocytoma cells.

S. Dubey et al., "Design, synthesis and characterization of some bioactive conjugates of curcumin with glycine, glutamic acid, valine and demethylenated piperic acid and study of their antimicrobial and antiproliferative properties," *Eur. J. Medicinal Chem.*, vol. 43, pp.1837-1846 (2008) discloses the synthesis of mono- and di-esters of curcumin with the moieties named in the paper's title, and the use of those mono- and di-esters against certain bacteria, fungi, and human cancer cell lines.

A 15-amino acid segment of the beta chain of chorionic gonadotropin (βCG) conjugated to a lytic peptide (e.g., βCG-Phor21 (ala)) has been shown to target and destroy prostate and breast cancer cells. See J. Lee et al., *J. Pharmacokinetics and Pharmacodynamics*, vol. 60, pp. 1-8 (2008); W. Hansel et al., "Conjugates of lytic peptides and LHRH or BetaCG target and cause necrosis of prostate cancers and metastases," *Mol. Cell. Endocrinol.*, vol. 269, pp. 26-33 (2007); and (3) W. Hansel et al., "Destruction of breast cancers and their metastases by lytic peptide conjugates in vitro and in vivo," *Mol. Cell. Endocrinol.*, vol. 260-262, pp. 183-9 (2007).

S. Dutta et al., "Enhanced antioxidant activities of metal conjugates of curcumin derivatives," *Metal Based Drugs*, vol. 8, pp. 183-188 (2001) discloses certain curcumin derivatives and copper conjugates, and their ability to scavenge free radicals.

J. Shim et al., "Hydrazinocurcumin, a novel synthetic curcumin derivative, is a potent inhibitor of endothelial cell proliferation," *Bioorganic & Medicinal Chemistry*, vol. 10, pp. 2987-2992 (2002) discloses the activity of curcumin and certain derivatives against angiogenesis.

Published United States patent application publication no. 2007/0060644 discloses certain curcumin derivatives, and their use against certain conditions including Alzheimer's disease, diabetes, cancer, inflammation, and other conditions.

U.S. Pat. No. 5,861,415 discloses anti-oxidant, anti-inflammatory, antibacterial, antifungal, antiparasitic, anti-mutagen, anticancer and detoxification properties of curcuminoids, including curcumin, demethoxy curcumin and bis demethoxy curcumin.

U.S. Pat. No. 5,891,924 discloses the use of curcumin to inhibit the activation of NfkB transcription factor, for example to treat toxic/septic shock or graft-versus-host reaction.

Published international patent application WO/2002/002582 discloses curcumin derivatives with improved water solubility, in which the curcumin is linked to a mono, oligo, or polysaccharide, and the use of these curcumin derivatives against cancer, chronic-inflammatory diseases, and diseases associated with a retrovirus infection.

It has been reported that uterine fibroids express LHRH receptor, and that LHRH, LHRH agonists, and LHRH antagonists may have an effect upon uterine fibroids. See N. Chegini et al., "Gonadotropin-releasing hormone (GnRH) and GnRH receptor gene expression in human myometrium and leiomyomata and the direct action of GnRH analogs on myometrial smooth muscle cells and interaction with ovarian steroids in vitro," *J. Clin. Endocrin. Metab.*, vol. 81, pp. 3215-3221 (1996); and M. Marinaccio et al., "The estimation of LHRH receptors in the tissue of human leiomyoma, myometrium and endometrium," *Minerva Ginecol.*, vol. 46, pp. 519-526 (1994, English language abstract).

DISCLOSURE OF THE INVENTION

We have discovered that conjugating LHRH to curcumin (LHRH-Curcumin) substantially enhances water solubility (as compared to native curcumin), targets the curcumin to cells expressing LHRHR, facilitates intravenous administration, and preserves the anti-cancer efficacy of curcumin while substantially enhancing its bioavailability at lower dosages. Without wishing to be bound by this hypothesis, it is believed that curcumin acts intracellularly both by inducing programmed cell death (apoptosis), and by inhibiting the growth of blood vessels (angiogenesis) in tumors. Curcumin does not appear to induce apoptosis in normal (noncancerous) cells. Thus, we hypothesize that LHRH-Curcumin targets and induces apoptosis in human pancreatic cancer cells and other cancer cells that express LHRH receptors, likely via inhibition of NF-kB. The LHRH decapeptide (and its analogs) can be used to target cell surface receptors so that anticancer drugs are delivered specifically to the cancer cells expressing the LHRH receptors: pancreas, prostate, breast, testicular, uterine, ovarian, melanoma.

The novel targeted therapy will be of great benefit for patients with advanced or metastatic pancreatic and other LHRHR-expressing or CG receptor-expressing tumors. LHRH-Curcumin or βCG-Curcumin (or analogs) will bind to the membrane receptors on cancer cells and be internalized by the cells, rendering the cancer cells more susceptible to apoptosis. The novel conjugates may be used to prevent, treat, or reduce the recurrence of cancer.

In an alternative embodiment, LH-Curcumin, CG-Curcumin, βLH-Curcumin, or βCG-Curcumin (or an analog, such as one employing a segment of the alpha or beta chain of CG or LH) is used in the treatment or prevention of cancers that express receptors for LH or CG, for example those of the prostate, breast, ovary, testis and uterus; and perhaps pancreatic and melanoma cancer cells as well. CG is a close homolog of LH.

The novel LHRH-curcumin conjugate is water-soluble and saline-soluble, and may readily be administered by intravenous injection or other route of injection. We hypothesize that the LHRH-Curcumin conjugate targets the LHRH membrane receptors on pancreatic cancer cells, is internalized, and interferes with intracellular signaling events in pancreatic cancer cells. The water solubility of the novel LHRH-curcumin conjugate is itself surprising, as previous attempts to make curcumin derivatives water-soluble have not been particularly successful. The solubility of the conjugate in saline (PBS) at room temperature is at least up to 1.2 mg per 50 µL (=24 g/L), although we have not yet tested the upper limit of solubility.

Completed and ongoing in vitro and in vivo animal trials in our laboratory demonstrate the efficacy of the LHRH-Curcumin conjugate against pancreatic cancer. Future clinical trials will be conducted in human cancer patients in accordance with applicable laws and regulations.

MODES FOR CARRYING OUT THE INVENTION

EXAMPLES 1-3

The following peptides were synthesized for comparison studies:

LHRH:
(SEQ ID NO 1)
pGlu-His-Trp-Ser-Tyr-Gly-Leu-Arg-Pro-Gly

Phor21 lytic peptide:
(SEQ ID NO 2)
Lys-Phe-Ala-Lys-Phe-Ala-Lys-Lys-Phe-Ala-Lys-Phe-
Ala-Lys-Lys-Phe-Ala-Lys-Phe-Ala-Lys LHRH-Phor21 conjugate:
(SEQ ID NO 3)
pGlu-His-Trp-Ser-Tyr-Gly-Leu-Arg-Pro-Gly-Lys-Phe-
Ala-Lys-Phe-Ala-Lys-Lys-Phe-Ala-Lys-Phe-Ala-Lys-
Lys-Phe-Ala-Lys-Phe-Ala-Lys The peptides were synthesized by a commercial peptide-synthesis facility, American Peptide Company, Inc (Sunnyvale, Calif., USA). The purity of each of the peptides was greater than 85%, as determined by reverse-phase high-performance liquid chromatography.

EXAMPLE 4

Design and Synthesis of LHRH-Curcumin Conjugate

Figure 1:
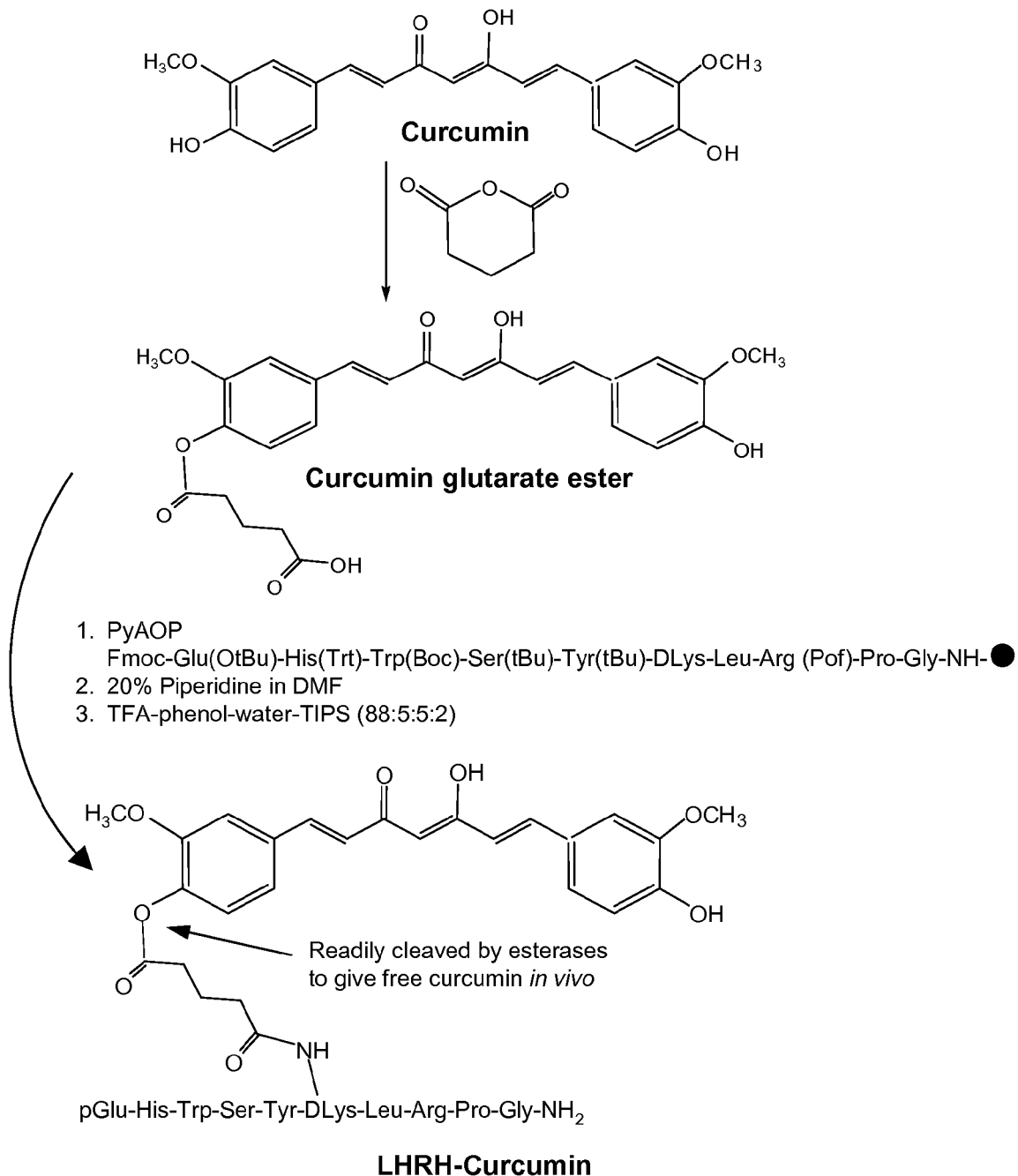
FIG. 1 depicts the synthesis of LHRH-curcumin.

All chemicals were purchased from Sigma Chemical Co. (St. Louis, Mo., USA) or from Fisher Scientific (NJ, USA). LHRH-Curcumin was synthesized at the Louisiana State University Peptide Facility. A prototype embodiment employed a glutarate ester linkage to covalently link the two components of the conjugate. Glutarate ester linkages yield derivatives that are stable in aqueous solution, but that will readily hydrolyze in the presence of an esterase to release the drug molecule at the delivery site. The reaction of Curcumin with glutaric anhydride in the presence of pyridine produced Curcumin glutarate ester. See FIG. 1. Coupling the Curcumin glutarate ester to [DLys$^6$]-LHRH, either in solution or during solid-phase synthesis, produced the LHRH-Curcumin conjugate. It is known that [DLys$^6$]-LHRH can readily be modified with large molecules at the epsilon amino side chain of the DLys$^6$ moiety, without compromising the ability to bind to LHRH receptors. Other linkers known in the art may also be used, preferably linkers having from 2 to 10 carbon atoms, for example, acetate linkers, short PEG chains, ester linkers, sugars, lectins, antibodies and their fragments, and hormones and hormone analogues.

Under dry conditions, a solution of curcumin (0.1 g, 0.271 mmol) in 1 mL of pyridine was stirred at room temperature for 30 min. The solution was treated with glutaric anhydride salt (0.028 g, 0.246 mmol) and stirred overnight at 60° C. The solution was concentrated by rotary evaporation, dissolved in $CH_2Cl_2$, and washed with 5% HCl. The organic fraction was dried over $MgSO_4$, and the solvent was removed by rotary evaporation. The solid product was dried in a desiccator for 8 hours to give dry Curcumin glutarate ester. Yield, 106 mg (90%). TOF-MS (ESI) 483.1657 (M+H$^+$), calculated MW=482.16.

LHRH-curcumin conjugate was synthesized by Fmoc solid phase chemistry techniques. H-Rink Amide ChemMatrix resin (0.52 mmol) was placed into a column. The resin was then washed with DMF in continuous-flow mode using a Pioneer Peptide Synthesizer. The side chain-protected amino acid derivatives used were, in sequence, Fmoc-Glu(OtBu)-OH, Fmoc-His(Trt)-OH, Fmoc-Trp(Boc)-OH, Fmoc-Ser(tBu)-OH, Fmoc-Tyr(tBu)-OH, Fmoc-D-Lys(Alloc)-OH. Fmoc-Leu-OH, Fmoc-Arg(Pbf)-OH, Fmoc-Pro-OH, and Boc-Gly-OH. The Alloc protecting group was removed using Pd(0), followed by double-coupling of curcumin glutarate ester. All couplings employed four equivalents of amino acid, malonate, PyAOP (and sometimes HOBT and TBTU), dissolved in 0.5M DIEA in DMF at room temperature to a final concentration of 0.25M. Intermediate products were washed between reactions with DMF. Minimal preactivation times were used. The Fmoc group was deprotected with 20% piperidine in DMF for 5 min.

Once peptide synthesis was compete, a 15 ml cocktail of TFA:phenol:water:TIPS (88:5:5:2) was added to the resin, and the mixture was agitated for 2.5 hours at room temperature. The mixture was then filtered, and the resin was washed with TFA (5 mL). The combined aqueous TFA solutions were extracted with $Et_2O$ and then freeze-dried. LHRH-Curcumin was purified by gel filtration using Sephadex LH-20, and purified samples were lyophilized and stored at −20° C. The LHRH-Curcumin was analyzed with a Hitachi MS-8000 3DQ LC-ion trap mass spectrometer with electrospray and APCI ionization methods. Yield, 0.12 g (48%), TOF-MS (ESI) 1717.7892 ($M+H^+$), calculated MW=1716.79.

EXAMPLE 5

LHRH Receptor is Expressed in Human Pancreatic Cancer Cell Lines

Pancreatic cell lines MIAPaCa-2, BxPC-3, and PANC-1 were obtained from the American Type Culture Collection. All cell lines were cultured in DMEM supplemented with 10% FBS, 100 units/mL penicillin, and 100 μg/mL streptomycin. The presence and location of LHRH-receptors in these pancreatic cancer cell lines was determined by immunochemical methods.

Confocal microscopy was used to visualize the location of LHRH receptors. Cells were plated in twelve-well tissue culture plates one day before observation, and then fixed with 2% formaldehyde. The fixed cells were washed with PBS. Membranes were partially permeabilized with 0.1% Trion-X100. The cells were incubated with 2% goat serum for an hour, and then incubated overnight at 4° C. with primary antibody specific for LHRH receptor (GnRH-R Ab03, Lab Vision Corporation, Fremont, Calif.). The cells were then washed with PBS, incubated for an hour with secondary antibody conjugated with Alexa Flour 488 (Molecular probes, Eugene, Oreg.), and washed again with PBS. The cells were mounted with mounting medium from Molecular Probes (Carlsbad, Calif.). The immunostained cells were imaged with an oil immersion objective (×40) and a confocal laser microscope (Zeiss Confocal LSM510, Carl Zeiss MicroImaging Inc., Thornwood, N.Y., USA) equipped with an argon-krypton laser. Skov3 ovarian cancer cells were used as negative controls, and MDA-MB-435 breast cancer cells were used as positive controls. LHRHR locations were indicated by green fluorescence, and nuclei by blue stain. Confocal laser scanning microscopy (not depicted here due to the difficulties in reproducing color photographs in a patent) clearly indicated that all three pancreatic cancer cell lines, as well as the positive control, but not the negative control, expressed LHRH receptor.

Standard SDS-PAGE and Western blotting procedures in cell extracts also clearly indicated the expression of LHRHR in the same three pancreatic cancer cell lines, as well as in positive control, but not in the negative control. (data not shown) Whole cell lysates were prepared from the same three pancreatic cancer cell lines, positive control, and negative control. The same amount of protein lysate was loaded in each lane, as determined by α-β Actin. The expression of LHRHR was detected by assay with monoclonal antibody against LHRHR (GnRH-R Ab01, Lab Vision Corporation, Fremont, Calif.). MDA-MB-435 or MCF-7 (breast cancer cell) lysates were used as positive controls, and Skov-3 (ovarian cancer cell) lysate or Chinese Hamster Ovary (CHO) cell lysate was used as negative control. The Western blot results clearly indicated the expression of LHRHR in pancreatic cancer cells.

EXAMPLE 6

Flow Cytometric Analysis of LHRH Receptor Expression

One million cells from each of the pancreatic cancer cell lines were collected and washed with PBS containing 1% FBS. The cells were then incubated on ice for 30 min with 10 μg/ml of monoclonal mouse antibody against LHRH receptor. The cells were washed twice with PBS containing 1% FBS, and then were further incubated for an additional 30 min on ice with Alexa Flour 488 (Molecular probes, Eugene, Oreg.), a goat anti-mouse secondary antibody conjugated to FITC. The cells were washed twice more, and suspended in 300 μl of PBS for flow cytometry. 10,000 events were collected on a FASCcalibur flow cytometer, and analyzed using Cellquest software (Becton Dickinson). Isotype controls were prepared similarly, except that an IgG1 antibody from Santa Cruz Biotechnology (Santa Cruz, Calif.) was used instead of an LHRH receptor antibody. Results showed that the LHRHR-mab specifically bound to the pancreatic cancer cell surfaces (data not shown).

EXAMPLE 7

Reverse Transcriptase-Polymerase Chain Reaction (RT-PCR)

LHRH receptor mRNA transcription in pancreatic cancer cells was confirmed by RT-PCR. Total RNA isolation was conducted with an RNA isolation kit (Ambion, Austin, Tex.). RT-PCR for the LHRH receptor and for $beta_2$-microglobulin (internal control) was performed with an Access RT-PCR system (Promega, Madison, Wis.). The amplified cDNA products were separated on a 1.5% agarose gel, stained with ethidium bromide, and sequenced. The primers for the LHRH receptor were: 5'-GACCTTGTCTGGAAAGATCC-3' (bp 93-112, SEQ ID NO. 4); and 5'-CAGGCTGATCACCAC-CATCA-3' (bp 392-411, SEQ ID NO 5). MDA-MB-435 and MCF-7 (breast cancer cells) were used as positive controls, and CHO (Chinese hamster ovary cells) were used as negative controls (data not shown).

EXAMPLE 8

Cytotoxicity Assay

Figure 2A:
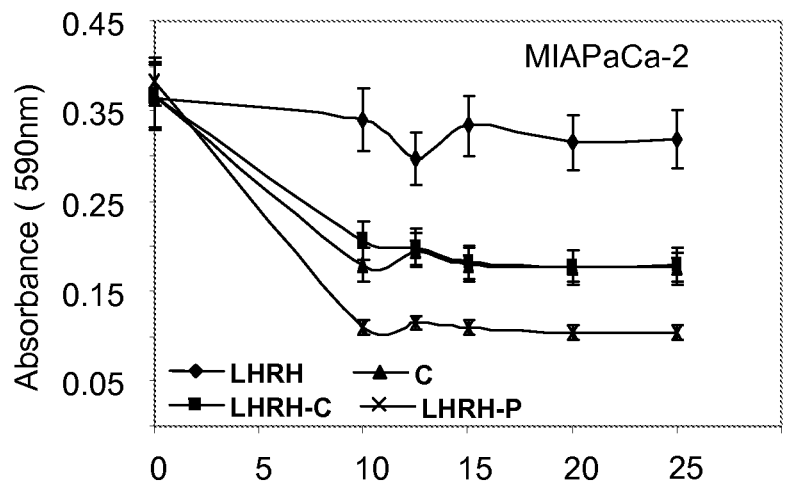
FIGS. 2(A)-2(C) depict the effects of LHRH-Phor21, LHRH-Curcumin, and Curcumin on the proliferation of three pancreatic cancer cell lines in vitro.
Figure 2B:
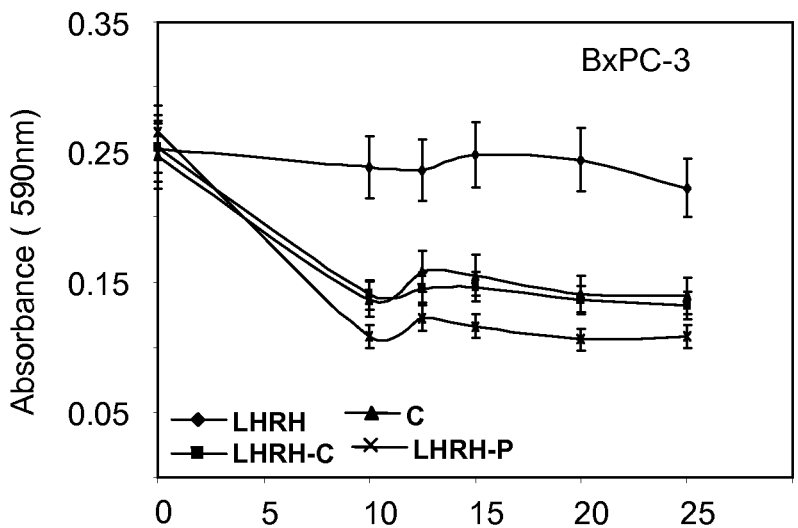
Figure 2C:
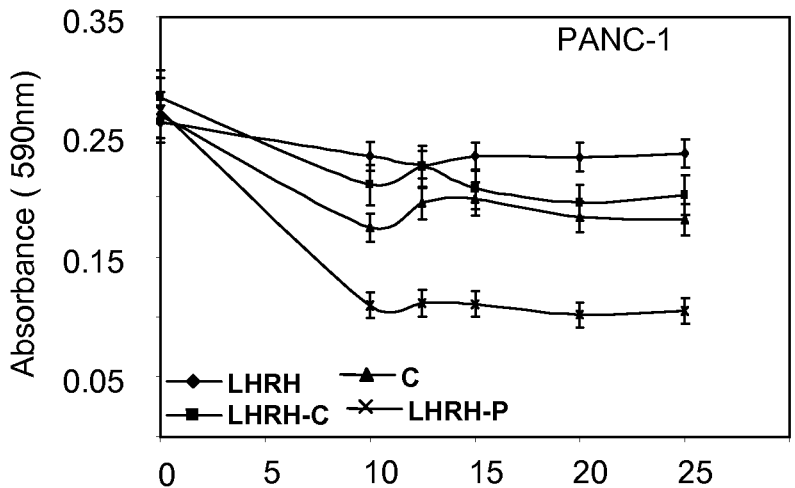

The cytotoxicity of the peptides was determined with a modified MTT (3-(4,5-dimethylthiazol-2-yl)-2,5-diphenyltetrazolium bromide) assay. Briefly, MIAPaCa-2, BxPC-3 and PANC-1 cells (2000/well) were separately incubated in 96-well plates in triplicate in a cell growth medium with different concentrations of LHRH, LHRH-Curcumin, Curcumin, and LHRH-Phor21. Three wells served as controls, each receiving an equivalent volume of medium. After 24 hours, an MTT solution (5 mg/ml in PBS) was added to each well and incubated for 2 hours at 37° C., followed by extraction with buffer (20% SDS and 50% dimethylformamide). The cells were incubated overnight at 37° C. Optical absorbance of the cell suspension was then measured at 590 nm using an MRX Revelation 96-well multiscanner (Dynex Technologies, Chantilly, Va.). From these measurements the IC50 doses of the peptides were calculated. We observed that LHRH-Phor21 (LHRH-P), LHRH-Curcumin (LHRH-C), and Curcumin (C) all inhibited the proliferation of pancreatic cancer cells. Results are shown in FIGS. 2(A)-2(C). Values given are mean±SD of triplicate cultures. The cytotoxicity of LHRH-C was almost equal to that of free Curcumin, while LHRH-Phor21 had greater cytotoxicity than that of LHRH-Curcumin.

EXAMPLE 9

Association of Cytotoxicity with Binding to LHRH Receptor

Figure 3A:
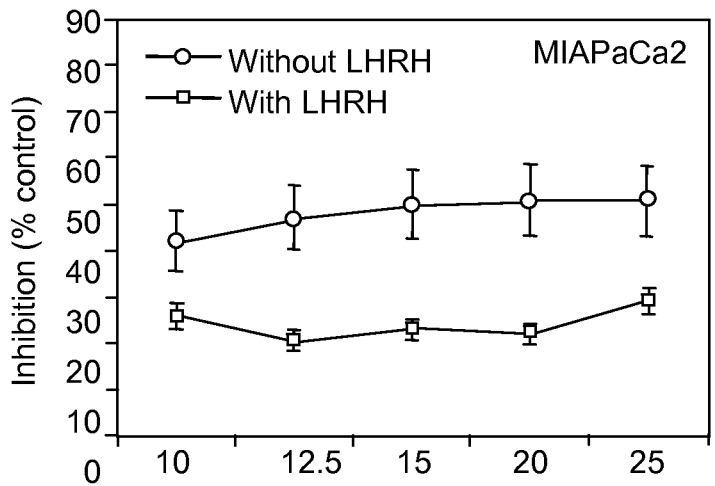
FIGS. 3(A)-3(C) depict cytotoxicities of LHRH and LHRH-curcumin against pancreatic cancer cells in a competitive binding assay.
Figure 3B:
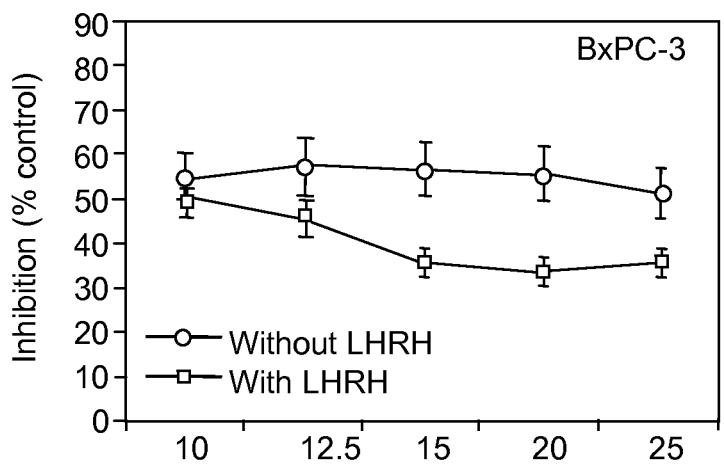
Figure 3C:
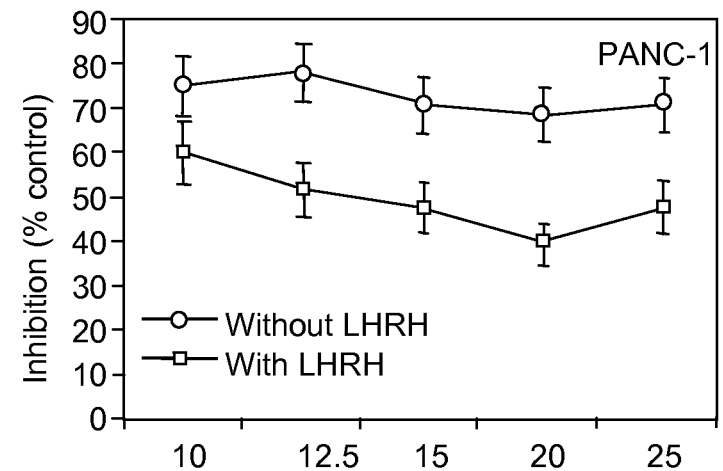

To verify that cytotoxicity of LHRH-Curcumin was associated with binding to LHRH receptor, we also co-incubated the cells with free LHRH peptide and LHRH-Curcumin in a competitive assay, and measured the cytotoxicities. Results are shown in FIGS. 3(A)-3(C). We observed that the effect of LHRH-Curcumin was indeed reduced by the presence of free LHRH peptide. These observations are consistent with a mechanism in which the LHRH-Curcumin preferentially affects cells expressing LHRH receptor by binding to the receptor. The cells, MIAPaCa-2, BxPC-3 and PANC-3 (2000 cells/0.1 ml) were incubated for 24 hours in triplicate with either medium or with the indicated dose of LHRH and a constant concentration of LHRH-Curcumin (15 µM). After 24 hours the cells were then assayed for inhibition of cell proliferation by the MTT method. The data were expressed as percentages of control; reproducibility was confirmed in four independent experiments.

EXAMPLE 10

Construction of Luciferase-Labeled Cells

We constructed stable pancreatic cell lines that express CMV-driven luciferase. The plasmid pGL4.17CMV-Luc was constructed from the enhanced synthetic firefly luciferase gene-carrying plasmid pGL4.17 (Luc2/Neo) and the CMV promoter-containing plasmid pRLCMV (Promega, U.S.A.). The CMV promoter was digested from pRLCMV using Bgl11 and Hind111, and inserted into the multiple cloning site of pGL4.17 (Luc2/Neo) to make the plasmid pGL4.17CMV-Luc. Eight to twelve hours before transfection, MIAPaCa-2 cells were seeded at 50% confluency in a 6-well plate with 2 ml culture medium per well. The MIAPaCa-2 cells were transfected with 2 µg of pGL4.17CMV-Luc per well using Superfect transfection reagent (Qiagen), following the manufacturer's recommended protocol. 2 µg of pGL4.17 (luc2/Neo) was simultaneously used in a separate well for transfection as a control, to prepare cells that were otherwise the same but lacking the CMV promoter. After 24 hours the cells were trypsinized, and plated over five, 5-cm dishes in a culture medium containing 0.3 mg/ml G418 (selection medium, Promega, Madison, Wis.). Clones were grown for 10 days, and the selection medium was renewed daily. Dishes containing 10-15 large colonies were trypsinized, and individual clones were re-suspended in 50 ml medium and added to 24-well plates containing selection medium. Selection medium was replaced daily until cells were confluent. To confirm luciferase induction, 24 confluent wells were trypsinized, and one well per clone was seeded in culture medium and incubated for 24 h. Non-transfected MIAPaCa-2 cells were used as controls. Medium was removed, and cells were lysed in luciferase cell culture lysis reagent. A 20 ml portion of cell lysate was added to a luminometer tube containing 100 ml of luciferase assay reagent. (Promega). Luciferase activity was measured with a FB 12 luminometer, with a 2-second measurement delay followed by a 10-second measurement. Clones with the highest expression of luciferase were used in further studies. A strong increase in luciferase expression was observed in the cells transfected with pGL4.17CMV-Luc, as compared to the relatively low background of luciferase seen with the expression vector pGL4.17-luc, lacking the CMV promoter (data not shown). Similar results were also seen with Western blot analysis for luciferase expression (data not shown).

In vivo Experiments

EXAMPLE 11

Pancreatic Tumor Model in Nude Mice

MIAPaCa-2, a cell line expressing the LHRH receptor, was then used for in vivo experiments. We stably transfected MIAPaCa-2 cells with a gene encoding luciferase. We used the transfected cells to produce a pancreatic cancer xenograft mouse model.

Forty-eight female nude mice (athymic Balb/c, 4-5 weeks old) were obtained from a commercial vendor (Charles River Laboratories, Wilmington, Mass.), and caged individually in a room maintained at constant temperature and humidity under a 12-h light and darkness cycle, and fed a regular, autoclaved chow diet with water ad libitum. The experimental protocol was reviewed and approved by the Institutional Animal Care and Use Committee at the Pennington Biomedical Research Center, Louisiana State University, Baton Rouge, La.

Luciferase-transfected MIAPaCa-2 cells were harvested from subconfluent cultures after a brief exposure to 0.25% trypsin and 0.2% EDTA. Trypsinization was stopped with medium containing 10% FBS. The cells were washed once in serum-free medium, and resuspended in PBS. Only suspensions containing suspended (non-adhering) cells, with >90% viability, were used for the injections. Tumors were established in mice by subcutaneous implantation of $1 \times 10^6$ luciferase-transfected MIAPaCa-2-luc cells with Matrigel™ (Collaborative Biomedical Products Becton Dickinson Labware, Bedford, Mass.) into the interscapular area in 0.1 ml PBS using a 27-gauge needle.

EXAMPLE 12

Treating Xenograft Tumors

After the tumors were established (100-250 mm$^3$), the 48 mice were randomized into six different treatment groups (n=8 mice per group): (1) LHRH alone, (2) LHRH-Curcumin, (3) LHRH-Phor21, (4) unconjugated LHRH and Phor21, (5) vehicle control, and (6) a control group of tumor-bearing mice that were necropsied before treatment (baseline controls). Treatments were administered by tail vein injections in 50 µl of normal saline twice a week for 3 weeks. Tumor volumes and mice body weights were measured twice weekly, and mice were necropsied one week after the last treatment. At necropsy, tumors, ovaries, kidneys, pancreases, lungs, spleen, several bones, and liver were removed and weighed, and metastatic cell numbers were measured by luciferase assay. The tumor volumes and weights were analyzed by one-way ANOVA, and compared among groups using an unpaired Student's t-test. Half of each tumor was fixed in formalin and embedded in paraffin for immunohistochemistry. The other half was flash-frozen in liquid nitrogen, and stored at −80° C. H&E staining was performed to confirm the presence of tumor(s) in each group. Tumor volumes were estimated by the standard formula: $V=\frac{1}{2}(x^2y)$, where x is the width and y is the length of the tumor.

EXAMPLE 13

Effect of LHRH-Curcumin on Human Pancreatic Cancer Xenograft

Figure 5A:
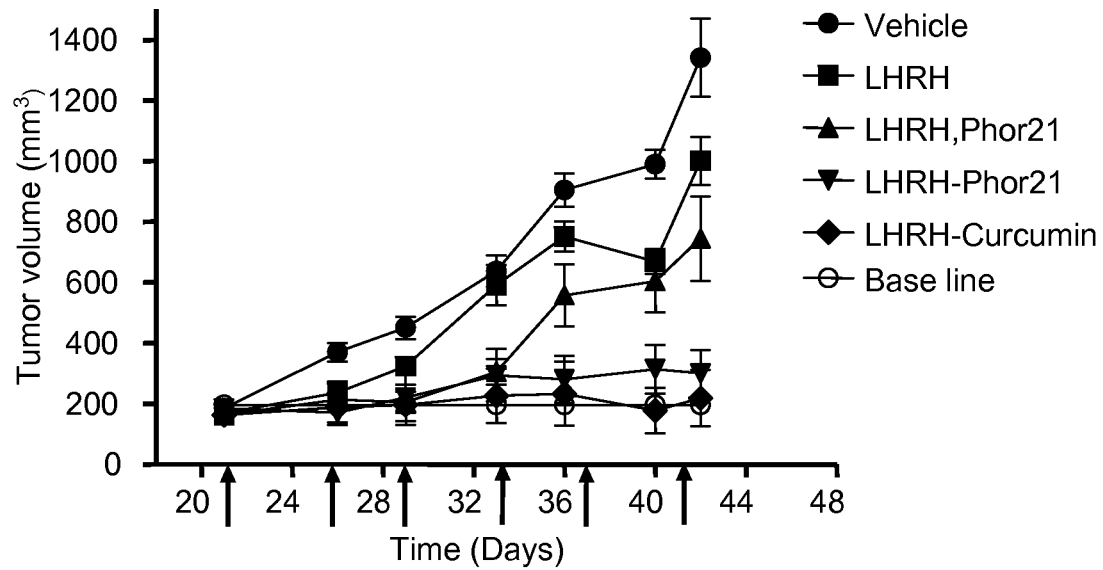
FIGS. 5(A)-5(D) compare in vivo effects of LHRH-Curcumin to those of LHRH-Phor21 against a human pancreatic cancer xenograft in female athymic nude mice.

As depicted in FIG. 5(A), with increasing time tumor volume increased in the saline-treated group while by day 44 the tumor volumes in the groups treated with LHRH-Curcumin and with LHRH-Phor21 were significantly lower (P<0.05) than those in the groups treated with LHRH or with vehicle, as determined by one-way ANOVA, although they were not significantly different from the tumor volumes of the baseline control group (at the P<0.05 level). Thus, both the LHRH-Curcumin conjugate and the LHRH-Phor21 conjugate caused complete cessation of growth of the pancreatic cancer cell xenografts. (The different dosages used for Phor21 and curcumin are not intended to be directly comparable. As a general observation, higher doses of curcumin conjugate may be used than lytic peptide conjugate, because curcumin has low toxicity while lytic peptides tend to have higher toxicities.) Group VI=base line data (sacrificed before the start of treatment to give base line data for tumor size). Arrows=treatment days. Points=mean. Vertical bars=SE.

Figure 5B:
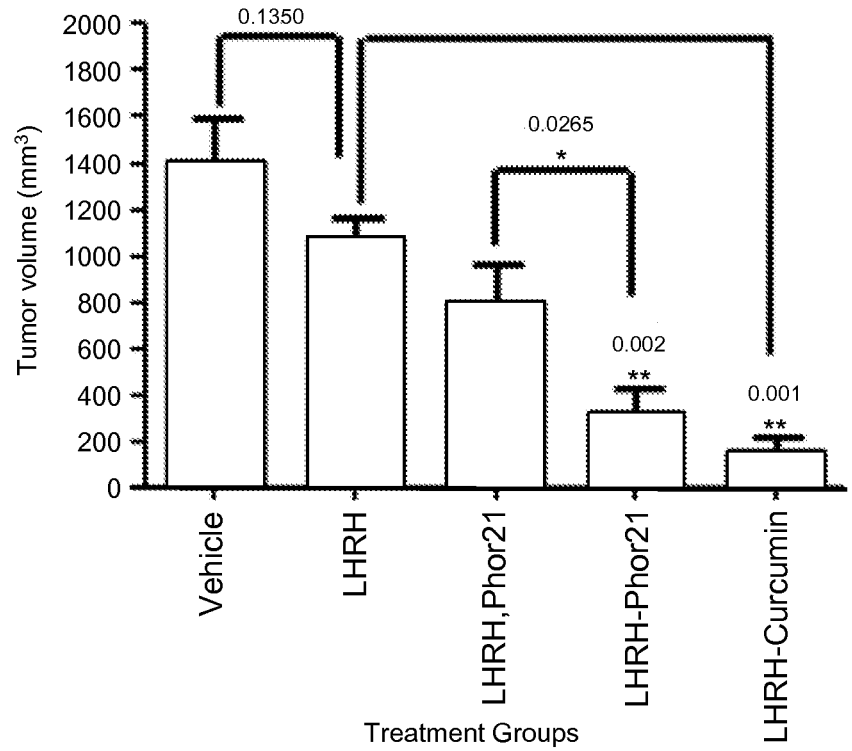
Figure 5C:
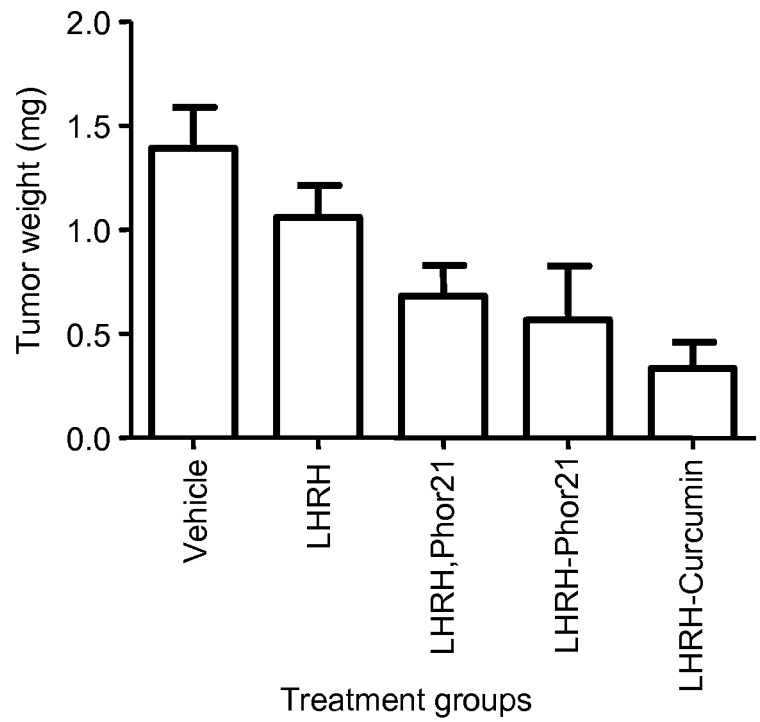

As shown in FIG. 5(B), final tumor volumes on day 47 for both the LHRH-Curcumin group and the LHRH-Phor21 group were significantly smaller than those for the vehicle group and the LHRH group (P<0.05). Similar results were seen for final tumor mass on day 47 (P<0.05) (FIG. 5(C)).

Figure 5D:
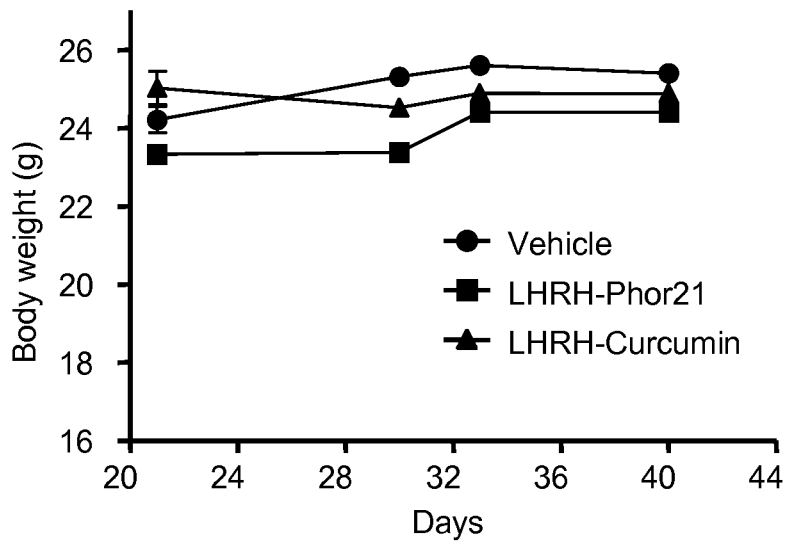

Mice body weights monitored as indicators of potential toxicity of LHRH-Curcumin and LHRH-Phor21 were not significantly different from control (P<0.05). See FIG. 5(D). No side effects were observed for either LHRH-Curcumin or LHRH-Phor21 in this study, except that some inflammation was seen in the mice tails at the site of injections with LHRH-Phor21.

EXAMPLE 14

Possible Mechanism of Action: Activation of Caspase 3

We have also investigated a possible mechanism of action. Without wishing to be bound by this hypothesis, our preliminary data support the view that LHRH-Curcumin induces apoptosis in cancer cells via the activation of caspases (cysteine-aspartic acid proteases).

An important step in apoptosis is the activation of caspase 3; therefore, we examined the effect of LHRH-Curcumin both on transcription of caspase 3 mRNA, and on total enzyme activity.

We measured transcription of the Caspase 3 coding sequence in pancreatic cancer cells (MIAPaCa-2) via the Reverse Transcriptase-Polymerase Chain Reaction (RT-PCR): Briefly, total RNA from one million cells, plated in triplicate was isolated with TRIzol reagent (Invitrogen, Carlsbad, Calif.). The initial cDNA was synthesized with a High Capacity cDNA Reverse Transcription kit (ABI, Foster City, Calif.) according to the manufacturer's protocol. The total RNA was treated with 2 μg of DNase I (Invitrogen, Carlsbad, Calif.), and then reverse-transcribed in a 20 μl reaction containing 1× buffer, 100 μM of each deoxynucleoside triphosphate (dNTP), 1× random primer, 5 U of RNase inhibitor, and 250 U of reverse transcriptase II. The reaction was carried out at 25° C. for 10 min, then at 37° C. for 2 hours, and then at 85° C. for 5 min. PCR amplification was then carried out with a GenAmp PCR System 2400 (Perkin-Elmer Instruments, Shelton, Conn.) for caspase 3 and $\beta_2$-microglobulin ($\beta_2$-m, internal control) with Taq Polymerase (Sigma Aldrich, St. Louis, Mo.). The primers for caspase 3 were: 5'-TGG AAT TGA TGC GTG ATG TT-3' (SEQ ID NO. 6) and 5'-GGC AGG CCT GAA TAA TGA AA-3' (SEQ ID NO. 7). The primers for $\beta_2$-m were: 5'-ACC CCC ACT GAA AAA GAT GA-3' (SEQ ID NO. 8) and 5'-ATC TTC AAA CCT CCA TGA TG-3' (SEQ ID NO. 9). The PCR reaction products were separated by gel electrophoresis, and then imaged. The observations clearly indicated higher transcription levels for caspase 3 in cells treated with LHRH-Curcumin than in either controls or in cells treated with LHRH alone (data not shown).

We also directly measured the effect of LHRH-curcumin on caspase 3 enzyme activity with the Apo-ONE homogenous caspase-3/7 assay kit (Promega, Madison, Wis.). This assay uses a profluorescent substrate with an optimized, bifunctional cell lysis/activity buffer. MIAPaCa-2 cells were treated in triplicate (10,000 cells per well) with the free peptide LHRH, or with the LHRH-Curcumin conjugate, in each case at a 5 μM concentration, and incubated for 24 hours. Following the 24 hour incubation, the Apo-ONE homogenous caspase-3/7 assay was performed according to the manufacturer's protocol. The buffer and 100 μL Apo-ONE caspase-3/7 assay reagent were mixed and added to the samples. Cells were then incubated for an additional hour prior to fluorescence measurements. Upon sequential cleavage and removal of the Asp-Glu-Val-Asp peptide (SEQ ID NO. 10) by caspase-3/7 activity, the rhodamine 110 leaving group became intensely fluorescent with excitation at 499 nm and an emission maximum at 512 nm. The excitation/emission was recorded on a FlexStation (Molecular Devices, Sunnyvale, Calif.) with softMax Pro version 4.8 software. The experiment was conducted in duplicate. Statistical significance was determined by a two-tailed Students t-test, using GraphPad Prism software version 5.0.

Figure 6:
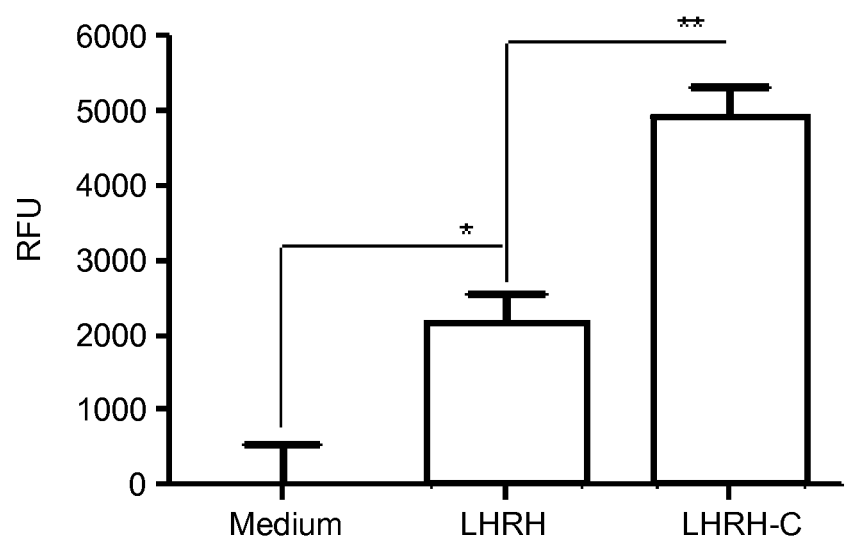
FIG. 6 depicts the effects of LHRH-curcumin and of LHRH on caspase 3 activity in pancreatic cancer cells.

As depicted in FIG. 6, treating the cells with LHRH alone significantly increased caspase-3/7 activity, as compared to the treatment with medium alone (p<0.05). Treating the cells with LHRH-Curcumin significantly increased caspase-3/7 activity, as compared to either medium or to the LHRH treatment alone (p<0.05). These results suggest that the LHRH-curcumin conjugate more strongly induces apoptosis in MIA-PaCa-2 cells, and by implication, in other pancreatic cancer cells and other cancer cells expressing the LHRH receptor.

EXAMPLE 15

Uterine Fibroids

Uterine fibroids, non-cancerous tumors of the uterus, often express LHRH receptors. Uterine fibroids may also be treated with the compositions of the present invention, specifically, conjugates of LHRH (or analog) with curcumin (or analog).

Miscellaneous

Unless otherwise noted, all experimental data reported in this specification are expressed or depicted as mean±standard deviation. Unless otherwise noted, comparison of mean values between different treatments was done by one-way ANOVA, followed by comparison among groups using Student's t-test. Differences are considered statistically significant at $p<0.05$.

In addition to LHRH (or CG or βCG) and curcumin, analogs of each component may also be used in conjugates in accordance with the present invention. Analogs of CG and LHRH, both agonists and antagonists, are well known in the art, and either may be used in practicing this invention. See, e.g., "Cancer chemotherapy based on targeting of cytotoxic peptide conjugates to their receptors on tumors," European Journal of Endocrinology (1999) 141:1-14. Antagonists of LHRH include, for example, Antide, Buserelin, Leuprolide acetate salt, [D-Ala$^6$]-LHRH, [D-Lys$^6$]-LHRH, [D-Trp$^6$]-LHRH, [Gln$^8$]-LHRH, [His(3-Methyl)$^2$]-LHRH, [des-Gly$^{10}$, D-Ala$^6$]-LHRH ethylamide, [des-Gly$^{10}$, D-His$^2$, D-Trp$^6$, Pro$^9$]-LHRH ethylamide, [des-Gly$^{10}$, D-His(Bzl)$^6$]-LHRH ethylamide, and [des-Gly$^{10}$, D-Phe$^6$]-LHRH ethylamide.

For analogs of curcumin and related compounds, see the review "Curcumin: From ancient medicine to current clinical trials," *Cellular and Molecular Life Sciences* 2008; 65: 1631-1652, and references 160, 161, 162, 169, and 171 from that review. See also Aggarwal S, Ichikawa H, Takada Y, Sandur S K, Shishodia S, Aggarwal B B, "Curcumin (diferuloylmethane) down-regulates expression of cell proliferation and antiapoptotic and metastatic gene products through suppression of I {kappa} B {alpha} kinase and AKT activation," *Mol Pharmacol* 2006; 69 (1):195-206; and U.S. Pat. No. 7,355,081; and published international application WO 2008/045534.

It has been reported that a portion of the curcumin molecule structure is essential for at least some of curcumin's physiological effects (desaturase inhibition). Therefore we believe that LHRH conjugated to that half of the curcumin molecule may also be an effective analog. See Kawashima H, Akimoto K, Jareonkitmongkol S, Shirasaka N, Shimizu S, "Inhibition of rat liver microsomal desaturases by curcumin and related compounds," *Biosci Biotechnol Biochem* 1996; 60 (1):108-10.

Following are a few of many examples of analogs of LHRH that have been reported in the literature:

S. Sealfon et al., "Molecular mechanisms of ligand interaction with the gonadotropin-releasing hormone receptor," *Endocrine Reviews*, vol. 18, pp. 180-205 (1997) is a review paper that, among other things, discusses the apparent role of each of the individual amino acids in the GnRH decapeptide, and gives extensive guidance on the types of substitutions that may be made in analogs. See particularly pp. 184-191 of this paper, and the schematic summary shown in FIG. 8 on page 190.

A 1986 review paper, M. Karten et al., "Gonadotropin-releasing hormone analog design. Structure-function studies toward the development of agonists and antagonists: rationale and perspective," *Endocrine Reviews*, vol. 7, pp. 44-66 (1986), described or gave citations to over 2000 GnRH analogs (p. 44, par. 1).

S. Sealfon et al., "The gonadotrophin-releasing hormone receptor: structural determinants and regulatory control," *Human Reproduction Update*, vol. 1, pp. 216-230 (1995) provides a review of contemporaneous knowledge of GnRH receptor structure and regulation of receptor expression. This review article mentions the fact that thousands of GnRH analogs have been synthesized and studied (p. 216).

M. Filicori, "Gonadotropin-releasing hormone agonists: a guide to use and selection," *Drugs*, vol. 48, pp. 41-58 (1994) is a review article discussing a number of GnRH agonists, and examples of the types of modifications that may be used to make such agonists. Among the examples mentioned are replacement of the tenth amino acid (glycine) of the native GnRH sequence with an ethylamide residue; or the substitution of the sixth amino acid residue (glycine) with other more lipophilic D-amino acids such as D-Phe, D-Leu, or D-Trp; or the incorporation of more complex amino acids in position 6, such as D-Ser (t-Bu), D-His (Bzl), or D-Nal (2); or in position 10, such as aza-Gly; or the N-Me-Leu modification in position 7 (see pp. 42 and 43). These modifications were said to result in more hydrophobic compounds that were more stable than the native GnRH molecule, and thus to have higher receptor affinity and in vitro potency. In addition, the more hydrophobic GnRH agonists were said to be more resistant to enzyme degradation, and to bind more strongly to plasma proteins and body tissues, thus decreasing renal excretion and prolonging drug half-life. This review article also discusses various routes of administration and delivery systems known in the art.

Another review article is P. Conn et al., "Gonadotropin-releasing hormone and its analogues," *New Engl. J. Med.*, vol. 324, pp. 93-103 (1991). Several GnRH analogs are disclosed including, as shown in Table 1 on p. 95, the analogs decapeptyl, leuprolide, buserelin, nafarelin, deslorelin, and histrelin; and several additional analogs discussed on p. 99.

A. Nechushtan et al., "Adenocarcinoma cells are targeted by the new GnRH-PE$_{66}$ chimeric toxin through specific gonadotropin-releasing hormone binding sites," *J. Biol. Chem.*, vol. 298, pp. 11597-11603 (1997) discloses a 67 kDa chimeric fusion protein comprising a *Pseudomonas*-derived toxin bound to a GnRH analog in which tryptophan replaced glycine as the sixth amino acid; as well as the use of that fusion protein to prevent the growth of colon carcinoma xenografts in nude mice, and to kill various adenocarcinoma cells in vitro.

G. Emons et al., "Growth-inhibitory actions of analogues of luteinizing hormone releasing hormone on tumor cells," *Trends in Endocrinology and Metabolism*, vol. 8, pp. 355-362 (1997) discloses that in vitro proliferation of two human ovarian cancer cell lines, and of two human endometrial cancer cell lines, was inhibited by the LHRH agonist triptorelin; and that in vitro proliferation of ovarian and endometrial cancer cell lines was also inhibited by the LHRH antagonist Cetrorelix; while against another ovarian cancer cell line the antagonist did not have this effect, although it partly blocked the antiproliferative effect of the agonist triptorelin. Antiproliferative effects of LHRH analogs against prostate cancer cell lines in vitro were also reported. This paper also reports that chronic administration of LHRH agonists inhibited ovarian or testicular function in a reversible manner.

M. Kovacs et al., "Recovery of pituitary function after treatment with a targeted cytotoxic analog of luteinizing hormone-releasing hormone," *Proc. Natl. Acad. Sci. USA*, vol. 94, pp. 1420-1425 (1997) discloses the use of a doxorubicin derivative conjugated to the carrier agonist [D-Lys$^6$] LHRH to reversibly (i.e., temporarily) inhibit gonadotrophic cells in the pituitary. It was also reported that this LHRH analog-toxin conjugate inhibited the growth of prostate tumors in rats.

J. Janovick et al., "Gonadotropin releasing hormone agonist provokes homologous receptor microaggregation: an early event in seven-transmembrane receptor mediated signaling," *Endocrinology*, vol. 137, pp. 3602-3605 (1996) discloses certain experiments using the agonist D-Lys$^6$-GnRH-lactoperoxidase conjugate, and others using the antagonist D-pGlu$^1$-D-Phe$^2$-D-Trp$^3$-D-Lys$^6$-GnRH-lactoperoxidase conjugate.

C. Albano et al., "Comparison of different doses of gonadotropin-releasing hormone antagonist Cetrorelix during controlled ovarian hyperstimulation," *Fertility and Sterility*, vol. 67, pp. 917-922 (1997) discloses experiments conducted with the GnRH antagonist Cetrorelix to determine the minimal effective dose to prevent premature LH surge in patients undergoing controlled ovarian hyperstimulation for assisted reproductive technologies.

L. Maclellan et al., "Superstimulation of ovarian follicular growth with FSH, oocyte recovery, and embryo production from Zebu (*Bos indicus*) calves: Effects of Treatment with a GnRH Agonist or Antagonist," *Theriogenology*, vol. 49, pp. 1317-29 (1998) describes experiments in which a GnRH agonist (deslorelin) or a GnRH antagonist (cetrorelix) were administered to calves to determine whether altering plasma LH concentration would influence follicular response to FSH and oocyte development.

A. Qayum et al., "The effects of gonadotropin releasing hormone analogues in prostate cancer are mediated through specific tumour receptors," *Br. J. Cancer*, vol. 62, pp. 96-99 (1990) discloses experiments investigating the use of the GnRH analog buserelin on prostate cancers.

A. Cornea et al., "Redistribution of $G_{q/11}\alpha$ in the pituitary gonadotrope in response to a gonadotropin-releasing hormone agonist," *Endocrinology*, vol. 139, pp. 397-402 (1998) discloses studies on the effect of buserelin, a metabolically stable GnRH agonist, on the distribution of the α-subunit of the guanyl nucleotide binding protein subfamily $G_{q/11}$.

See also: (i) European Patent EP0277829; (ii) Genaro G, Lacerda Neto J C, Rosa e Silva A A, "LH response (in vivo and in vitro) to an LHRH agonist administered to domestic male cats," *Arch Physiol Biochem* 2003; 111 (3):254-8; (iii) Horvath J E, Bajo A M, Schally A V, Kovacs M, Herbert F, Groot K, "Effects of long-term treatment with the luteinizing hormone-releasing hormone (LHRH) agonist Decapeptyl and the LHRH antagonist Cetrorelix on the levels of pituitary LHRH receptors and their mRNA expression in rats," *Proc Natl Acad Sci USA* 2002; 99 (23):15048-53; (iv) Wu T J, Mani S K, Glucksman M J, Roberts J L, "Stimulation of luteinizing hormone-releasing hormone (LHRH) gene expression in GT1-7 cells by its metabolite, LHRH-(1-5)," *Endocrinology* 2005; 146 (1):280-6.

The following LHRH analogs are available commercially, for example, from Aldrich: Luteinizing hormone releasing hormone human acetate salt; Luteinizing hormone releasing hormone salmon; [D-Ala$^6$, N-Me-Leu$^7$]-LH-RH; [D-Ala$^6$]-LH-RH acetate salt hydrate; [D-His(benzyl)$^6$]-LH-RH Fragment 3-9 ethylamide trifluoroacetate salt; [D-His(Bzl)$^6$]-LH-RH Fragment 1-7; [D-His(Bzl)$^6$]-LH-RH Fragment 2-9; [D-His(Bzl)$^6$]-LH-RH Fragment 4-9 ethylamide trifluoroacetate salt; [D-His(Bzl)$^6$]-LH-RH Fragment 5-9 Ethylamide trifluoroacetate salt; [D-Lys$^6$]-LH-RH; [D-pGlu$^1$, D-Phe$^2$, D-Trp$^{3,6}$]-LH-RH; [D-Ser$^4$]-LH-RH; [D-Trp$^6$]-LH-RH; [D-Trp$^6$]-LH-RH-Leu-Arg-Pro-Gly-NH$_2$; [des-Gly$^{10}$, D-Ala$^6$]-LH-RH ethylamide acetate salt hydrate; [des-Gly$^{10}$, D-His(Bzl)$^6$]-LH-RH ethylamide; [des-Gly$^{10}$, D-His$^2$, D-Trp$^6$, Pro$^9$]-LH-RH ethylamide trifluoroacetate salt; [des-Gly$^{10}$, D-Phe$^6$]-LH-RH ethylamide; [des-Gly$^{10}$, D-Ser$^4$, D-His(Bzl)$^6$, Pro$^9$]-LH-RH ethylamide acetate salt; [des-Gly$^{10}$, D-Ser$^4$, D-Trp$^6$, Pro$^9$]-LH-RH ethylamide trifluoroacetate salt; [des-Gly$^{10}$, D-Trp$^6$, D-Leu$^7$, Pro$^9$]-LH-RH ethylamide trifluoroacetate salt; [des-Gly$^{10}$, D-Trp$^6$]-LH-RH ethylamide; [des-Gly$^{10}$, D-Tyr$^5$, D-Trp$^6$, Pro$^9$]-LH-RH ethylamide trifluoroacetate salt ; [des-pGlu$^1$]-LH-RH ; [His(3-Methyl)$^2$]-LH-RH; [Hyp$^9$]-LH-RH; Formyl-[D-Trp$^6$]-LH-RH Fragment 2-10; LH-RH Fragment 1-2; LH-RH Fragment 1-4; Luteinizing hormone releasing hormone Fragment 4-10; Luteinizing hormone releasing hormone Fragment 7-10 dihydrochloride; Buserelin; Leuprolide acetate salt; [D-Trp$^6$]-LHRH Fragment, 1-6; and Antide.

Following are a few of many examples of analogs of CG, LH, or their beta subunits that have been reported in the literature:

Luteinizing hormone and chorionic gonadotropin are structurally and functionally homologous peptides. See, e.g., J. Lin et al., "Increased expression of luteinizing hormone/human chorionic gonadotropin receptor gene in human endometrial carcinomas," *J. Clinical Endocrinology & Metabolism*, vol. 79, pp. 1483-1491 (1994).

D. Morbeck et al., "A receptor binding site identified in the region 81-95 of the β-subunit of human luteinizing hormone (LH) and chorionic gonadotropin (hCG)," *Molecular & Cellular Endocrinology*, vol. 97, pp. 173-181 (1993) discloses experiments in which two series of overlapping peptides (each 15 residues in length), comprising the entire sequences of the β-subunits of human lutropin (LH) and chorionic gonadotropin (hCG), were used to identify all linear regions of the subunit that participate in the binding of the hormone to the receptor. The most potent inhibitor in a competitive binding assay was a peptide containing residues 81-95 of hCG. In addition, other regions that inhibited binding were identified. A third set of peptides was prepared in which each residue of the 81-95 hCG sequence was sequentially replaced by alanine, to identify the more important residues for binding. Five such residues were identified as being important to binding. In addition to identifying the 81-95 hCG sequence as itself being a useful analog, this detailed information is useful in designing analogs of the beta subunit of luteinizing hormone or of chorionic gonadotropin.

V. Garcia-Campayo et al., "Design of stable biologically active recombinant lutropin analogs," *Nature Biotechnology*, vol. 15, pp. 663-667 (1997) describes the synthesis of a luteinizing hormone analog, in which the α and β subunits were fused through a linker. The analog was found to be biologically active, and to have significantly greater in vitro stability than the native heterodimer.

T. Sugahara et al., "Biosynthesis of a biologically active single peptide chain containing the human common a and chorionic gonadotropin β subunits in tandem," *Proc. Natl. Acad. Sci. USA*, vol. 92, pp. 2041-2045 (1995) describes the production of a chimeric peptide, in which the α and β subunits of human chorionic gonadotropin were fused into a single polypeptide chain. The resulting molecule was found to be efficiently secreted, and to show increased activity both in vitro and in vivo.

D. Puett et al., "The tie that binds: Design of biologically active single-chain human chorionic gonadotropins and a gonadotropin-receptor complex using protein engineering," *Biol. Repro.*, vol. 58, pp. 1337-1342 (1998) is a review of numerous published papers concerning human chorionic gonadotropin and its analogs, including the effects of chemical modifications, synthetic peptides, limited proteolysis, protein engineering to produce hormone chimeras, site-directed mutagenesis, and specific amino acid residues.

Y. Han et al., "hCGβ Residues 94-96 alter LH activity without appearing to make key receptor contacts," *Mol. Cell. Endocrin.*, vol. 124, pp. 151-161 (1996) describes the effects on LH activity of several particular amino acid substitutions in the beta subunit of LH (namely, at residues 94-96). Not only are numerous analogs specifically described in this paper, but this type of information provides important guidance to one of skill in the art in designing other analogs.

Z. Zalesky et al, "Ovine luteinizing hormone: Isoforms in the pituitary during the follicular and luteal phases of the estrous cycle and during anestrus," *J. Anim. Sci.*, vol. 70, pp.

3851-3856 (1992) discloses thirteen isoforms of LH in ewes. Each of these thirteen isoforms could be considered an analog of LH.

A. Hartee, "Multiple forms of pituitary and placental gonadotropins," pp. 147-154 in S. Milligan (Ed.), Oxford Reviews of Reproductive Biology (1989) discloses different glycoprotein variants that may be considered analogs of FSH, LH, and CG. Seven isoforms of LH, and six isoforms of hCG were isolated; all had bioactivity in vivo.

It has been reported that substitution of hFSH residues between hCG β-subunit cysteines 11-12 creates a bifunctional analog that binds FSHR and LHR or CGR. CG/LH analogs include: hCG/hFSH chimera containing FSH β-subunit residues between 101 and 109, truncated after β-subunit amino acid 114; CF39-58, hCG/hFSH chimera containing FSH β-subunit residues between 39 and 58; CF94-97, hCG/hFSH chimera containing FSH β-subunit residues between 94 and 97; CF94-117, hCG/hFSH chimera containing FSH β-subunit residues between 94 and 117, truncated after β-subunit amino acid 117; CL, hCG/hLH chimera containing hLH β-subunit residues 2-15 and 89-98; CL2-15, hCG/hLH chimera containing hLH β-subunit residues 2-15; CL42-48, hCG/hLH chimera containing hLH β-subunit residues 42-58; CL77-98, hCG/hLH chimera containing hLH β-subunit residues 77-98; CL98-121, hCG/hLH chimera containing hLH β-subunit residues 98-121, truncated at residue 121; CLF, chimera of CL and FSH containing FSH β-subunit residues between 101 and 109, truncated after β-subunit amino acid 114. See Wang Y, Bernard M P, Moyle W R. Bifunctional hCG analogs adopt different conformations in LH and FSH receptor complexes. Mol Cell Endocrinol 2000; 170 (1-2):67-77. See also U.S. Pat. No. 5,811,390.

Figure 4A:
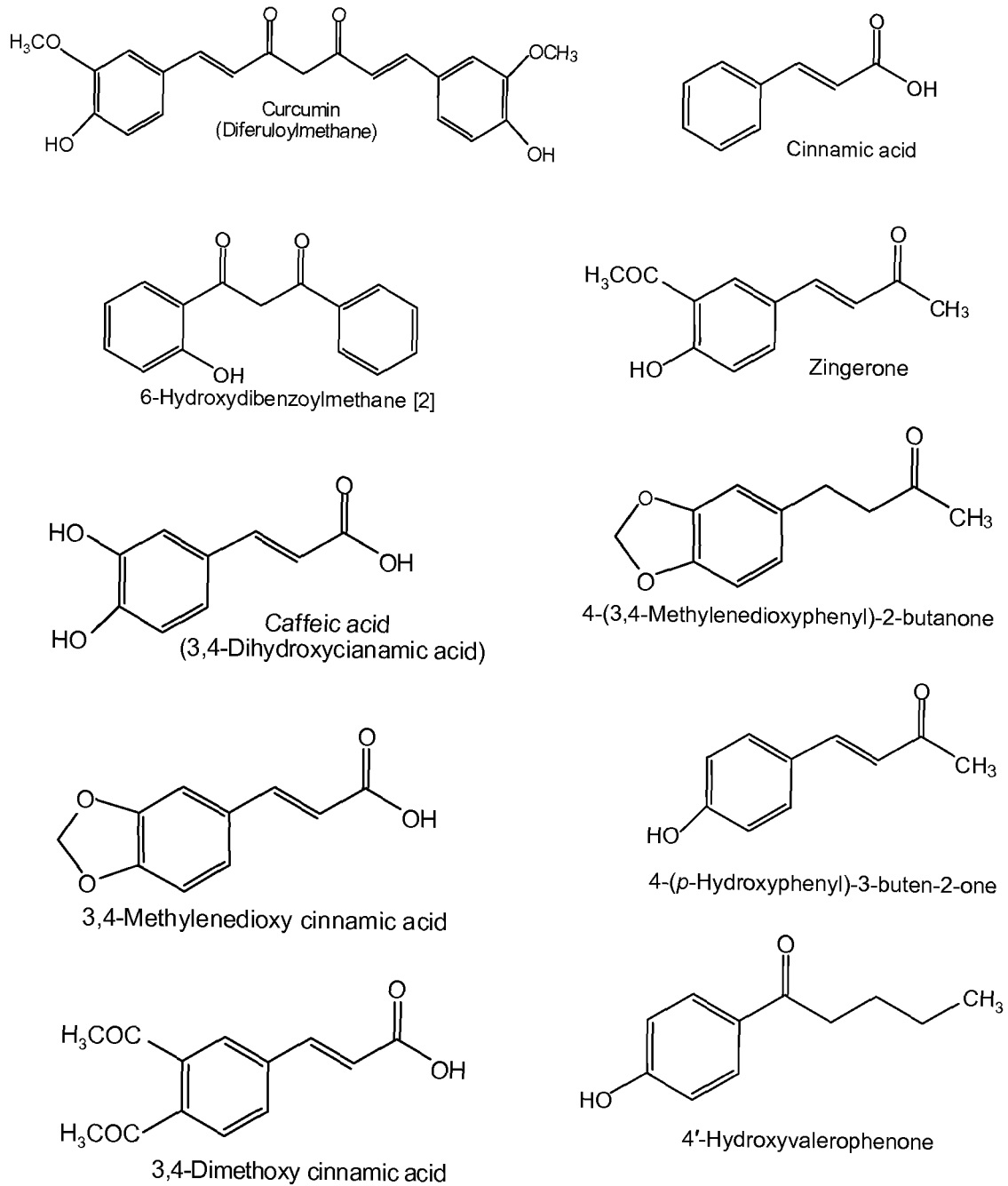
FIGS. 4A and 4B depicts several curcumin analogs.
Figure 4B:
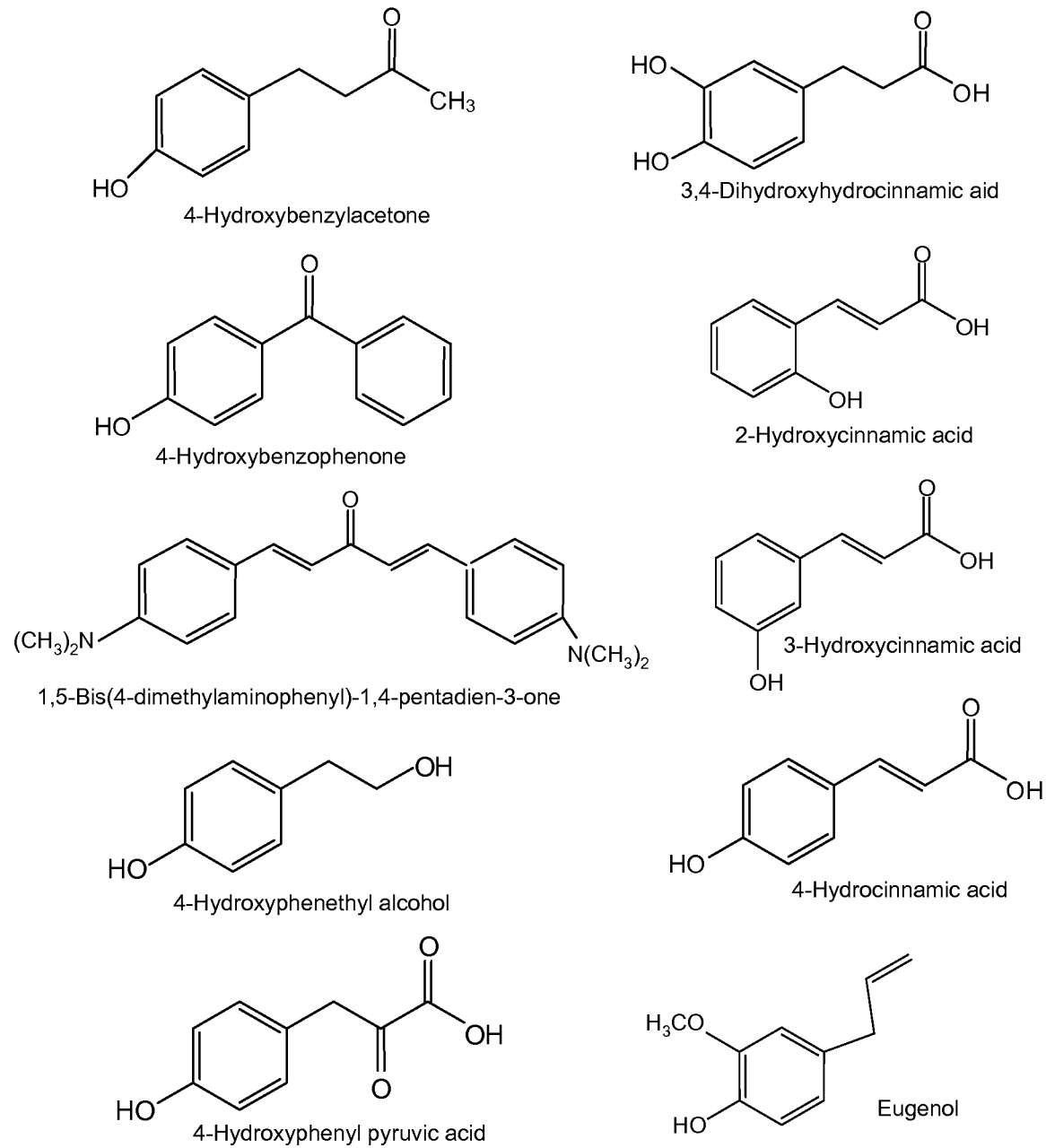

Some curcumin analogs are depicted in FIGS. 4A and 4B. Other references that disclose Curcumin conjugates and derivatives include those discussed in the earlier, background section of the present PCT Description; and each of the following:

(i) Nakagawa-Goto, K.; Yamada, K.; Nakamura, S.; Chen, T.-H.; Chiang, P.-C.; Bastow, K. F.; Wang, S.-C.; Spohn, B.; Hung, M.-C.; Lee, F.-Y.; Lee, F.-C.; Lee, K.-H., "Antitumor agents. Syntheses and evaluation of dietary antioxidant-taxoid conjugates as novel cytotoxic agents," *Bioorganic & Medicinal Chemistry Letters* 2007; 17:5204-5209.

(ii) Liu, J.; Jiang, F., "Design, synthesis, and primary evaluation on curcumin derivative as prodrugs of antitumor, "*Zhongguo Yaoshi* (Wuhan, China) 2005; 8:543-545.

(iii) Rieks, A.; Kaehler, M.; Kirchner, U.; Wiggenhorn, K.; Kinzer, M., "Preparation of novel curcumin/tetrahydrocurcumin derivatives for use in cosmetics, pharmaceuticals and for nutrition," WO 2004/03112.

(iv) Rieks, A.; Kaehler, M.; Kirchner, U.; Wiggenhorn, K.; Kinzer, M., "Preparation of curcumin esters for use in cosmetics, pharmaceuticals, and food additives," German patent application DE10245988A1.

(v) Scaramuzzino, G., "Preparation of nitrate prodrugs able to release nitric oxide in a controlled and selective way and their use for prevention and treatment of inflammatory, ischemic and proliferative diseases," European patent 1336602.

(vi) Sethi, S. C.; Rao, B. C. S., "Coloration of vanaspati," *Indian Journal of Technology* 1964; 2:208.

Following successful completion of animal trials, the LHRH-curcumin conjugate (or analog) is tested in human patients with pancreatic cancers (and other cancers expressing LHRH receptors) in clinical trials conducted in compliance with applicable laws and regulations. Following successful completion of animal trials, βLH-curcumin (or analog) will be tested in human patients with prostate cancers (and other cancers expressing LH receptors) in clinical trials conducted in compliance with applicable laws and regulations.

A compound that is a "conjugate" of two domains refers to a compound in which the two domains (or moieties) are covalently bonded to one another, either directly or via a linker.

Compounds used in the present invention may be administered to a patient by any suitable means, including intravenous, parenteral, subcutaneous, intrapulmonary, and intranasal administration. Parenteral infusions include intramuscular, intravenous, intraarterial, or intraperitoneal administration. The compounds may also be administered transdermally, for example in the form of a slow-release subcutaneous implant. They may also be administered by inhalation.

Pharmaceutically acceptable carrier preparations include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampoule, each containing a unit dose amount, or in the form of a container containing multiple doses.

A compound in accordance with the present invention may be formulated into therapeutic compositions as pharmaceutically acceptable salts. These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

A method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in nanoparticles or microcapsules by techniques otherwise known in the art including, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

As used herein, an "effective amount" of a compound is an amount, that when administered to a patient (whether as a single dose or as a time course of treatment) inhibits or reduces the growth of targeted tumors to a clinically significant degree; or alternatively, to a statistically significant degree as compared to control. "Statistical significance" means significance at the P<0.05 level, or such other measure of statistical significance as would be used by those of skill in the art of biomedical statistics in the context of a particular type of treatment or prophylaxis.

All references cited in this specification are hereby incorporated by reference in their entirety, as are the entire disclosures of the two provisional U.S. patent applications from which priority is being claimed. In the event of an otherwise irreconcilable conflict, the present specification shall control.

What is claimed:
1. A compound having the structure:
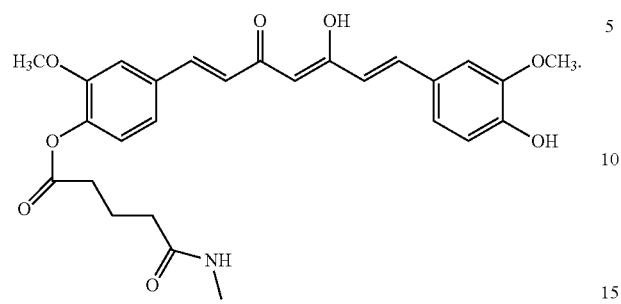
pGlu-His-Trp-Ser-Tyr-DLys-Leu-Arg-Pro-Gly-NH$_2$
* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa in position 1 is pyroGlu.  Luteinizing
      hormone releasing hormone (LHRH).

<400> SEQUENCE: 1

Xaa His Trp Ser Tyr Gly Leu Arg Pro Gly
1               5                   10

<210> SEQ ID NO 2
<211> LENGTH: 21
<212> TYPE: PRT
<213> ORGANISM: Artificial sequence
<220> FEATURE:
<223> OTHER INFORMATION: Phor21 lytic peptide

<400> SEQUENCE: 2

Lys Phe Ala Lys Phe Ala Lys Lys Phe Ala Lys Phe Ala Lys Lys Phe
1               5                   10                  15

Ala Lys Phe Ala Lys
            20

<210> SEQ ID NO 3
<211> LENGTH: 31
<212> TYPE: PRT
<213> ORGANISM: Artificial sequence
<220> FEATURE:
<223> OTHER INFORMATION: LHRH-Phor21 conjugate
<220> FEATURE:
<221> NAME/KEY: MOD_RES
<222> LOCATION: (1)..(1)
<223> OTHER INFORMATION: Xaa in position 1 is pyroGlu

<400> SEQUENCE: 3

Xaa His Trp Ser Tyr Gly Leu Arg Pro Gly Lys Phe Ala Lys Phe Ala
1               5                   10                  15

Lys Lys Phe Ala Lys Phe Ala Lys Lys Phe Ala Lys Phe Ala Lys
            20                  25                  30

<210> SEQ ID NO 4
<211> LENGTH: 20
<212> TYPE: DNA
<213> ORGANISM: Artificial sequence
<220> FEATURE:
<223> OTHER INFORMATION: Primer for LHRH receptor

<400> SEQUENCE: 4
gaccttgtct ggaaagatcc                                              20

<210> SEQ ID NO 5
```

-continued

```
<211> LENGTH: 20
<212> TYPE: DNA
<213> ORGANISM: Artificial sequence
<220> FEATURE:
<223> OTHER INFORMATION: Primer for LHRH receptor

<400> SEQUENCE: 5
caggctgatc accaccatca                                                 20

<210> SEQ ID NO 6
<211> LENGTH: 20
<212> TYPE: DNA
<213> ORGANISM: Artificial sequence
<220> FEATURE:
<223> OTHER INFORMATION: Primer for caspase 3

<400> SEQUENCE: 6
tggaattgat gcgtgatgtt                                                 20

<210> SEQ ID NO 7
<211> LENGTH: 20
<212> TYPE: DNA
<213> ORGANISM: Artificial sequence
<220> FEATURE:
<223> OTHER INFORMATION: Primer for caspase 3

<400> SEQUENCE: 7
ggcaggcctg aataatgaaa                                                 20

<210> SEQ ID NO 8
<211> LENGTH: 20
<212> TYPE: DNA
<213> ORGANISM: Artificial sequence
<220> FEATURE:
<223> OTHER INFORMATION: Primer for beta 2-microglobulin

<400> SEQUENCE: 8 accccccactg aaaaagatga                                                20

<210> SEQ ID NO 9
<211> LENGTH: 20
<212> TYPE: DNA
<213> ORGANISM: Artificial sequence
<220> FEATURE:
<223> OTHER INFORMATION: Primer for beta 2-microglobulin

<400> SEQUENCE: 9
atcttcaaac ctccatgatg                                                 20

<210> SEQ ID NO 10
<211> LENGTH: 4
<212> TYPE: PRT
<213> ORGANISM: Artificial sequence
<220> FEATURE:
<223> OTHER INFORMATION: Product of caspase 3 cleavage

<400> SEQUENCE: 10

Asp Glu Val Asp
1
```